US011191966B2

(12) United States Patent
Wah

(10) Patent No.: US 11,191,966 B2
(45) Date of Patent: Dec. 7, 2021

(54) FEEDBACK CONTROL OF NEUROMODULATION

(71) Applicant: Saluda Medical Pty Ltd, Artarmon (AU)

(72) Inventor: James Hamilton Wah, Artarmon (AU)

(73) Assignee: Saluda Medical Pty Ltd, Artarmon (AU)

( * ) Notice: Subject to any disclaimer, the term of this patent is extended or adjusted under 35 U.S.C. 154(b) by 0 days.

(21) Appl. No.: 16/091,428

(22) PCT Filed: Apr. 5, 2017

(86) PCT No.: PCT/AU2017/050296
§ 371 (c)(1),
(2) Date: Oct. 4, 2018

(87) PCT Pub. No.: WO2017/173493
PCT Pub. Date: Oct. 12, 2017

(65) Prior Publication Data
US 2019/0168000 A1 Jun. 6, 2019

(30) Foreign Application Priority Data
Apr. 5, 2016 (AU) ................ 2016901264

(51) Int. Cl.
*A61N 1/36* (2006.01)
*A61B 5/00* (2006.01)
(Continued)

(52) U.S. Cl.
CPC ........ *A61N 1/36132* (2013.01); *A61B 5/0031* (2013.01); *A61B 5/24* (2021.01);
(Continued)

(58) Field of Classification Search
CPC .... A61N 1/0551; A61N 1/18; A61N 1/36067; A61N 1/36071; A61N 1/36075;
(Continued)

(56) References Cited

U.S. PATENT DOCUMENTS

| 3,724,467 A | 4/1973 | Avery et al. |
| 3,736,434 A | 5/1973 | Darrow |

(Continued)

FOREIGN PATENT DOCUMENTS

| AU | 2013277009 B2 | 1/2016 |
| CN | 103648583 A | 3/2014 |

(Continued)

OTHER PUBLICATIONS

Extended European Search Report for European Application No. 16802237.4, Search completed Dec. 11, 2018, dated Dec. 19, 2018, 9 Pgs.

(Continued)

*Primary Examiner* — Christopher A Flory
(74) *Attorney, Agent, or Firm* — KPPB LLP

(57) ABSTRACT

An automated method of controlling neural stimulation. A neural stimulus is applied to a neural pathway in order to give rise to an evoked action potential on the neural pathway, and the stimulus is defined by at least one stimulus parameter. A neural compound action potential response evoked by the stimulus is measured. From the measured evoked response a feedback variable such as observed ECAP voltage (V) is derived. A feedback loop is completed by using the feedback variable to control the at least one stimulus parameter value for a future stimulus. The method adaptively compensates for changes in a gain of the feedback loop caused by electrode movement relative to the neural pathway. A compensating transfer function is applied to the feedback variable, the compensating transfer function (Continued)

being configured to compensate for both (i) a distance-dependent transfer function of stimulation, and (ii) a distance dependent transfer function of measurement which is distinct from (i).

18 Claims, 9 Drawing Sheets

(51) Int. Cl.
  *A61N 1/18* (2006.01)
  *A61N 1/372* (2006.01)
  *A61N 1/378* (2006.01)
  *A61B 5/24* (2021.01)
  *A61N 1/05* (2006.01)

(52) U.S. Cl.
  CPC .......... *A61B 5/4836* (2013.01); *A61N 1/0551* (2013.01); *A61N 1/18* (2013.01); *A61N 1/36067* (2013.01); *A61N 1/36071* (2013.01); *A61N 1/36075* (2013.01); *A61N 1/36139* (2013.01); *A61N 1/3787* (2013.01); *A61N 1/37264* (2013.01)

(58) Field of Classification Search
  CPC ............ A61N 1/36132; A61N 1/36139; A61N 1/37264; A61N 1/3787; A61B 5/0031; A61B 5/04001; A61B 5/4836
  See application file for complete search history.

(56) References Cited

U.S. PATENT DOCUMENTS

| | | |
|---|---|---|
| 3,817,254 A | 6/1974 | Maurer |
| 3,898,472 A | 8/1975 | Long |
| 4,158,196 A | 6/1979 | Crawford, Jr. |
| 4,418,695 A | 12/1983 | Buffet |
| 4,474,186 A | 10/1984 | Ledley et al. |
| 4,628,934 A | 12/1986 | Pohndorf et al. |
| 4,807,643 A | 2/1989 | Rosier |
| 4,856,525 A | 8/1989 | Van Den Honert |
| 5,113,859 A | 5/1992 | Funke |
| 5,139,020 A | 8/1992 | Koestner et al. |
| 5,143,081 A | 9/1992 | Young et al. |
| 5,156,154 A | 10/1992 | Valenta, Jr. et al. |
| 5,172,690 A | 12/1992 | Nappholz et al. |
| 5,184,615 A | 2/1993 | Nappholz et al. |
| 5,188,106 A | 2/1993 | Nappholz et al. |
| 5,215,100 A | 6/1993 | Spitz |
| 5,324,311 A | 6/1994 | Acken |
| 5,417,719 A | 5/1995 | Hull et al. |
| 5,431,693 A | 7/1995 | Schroeppel |
| 5,458,623 A | 10/1995 | Lu et al. |
| 5,476,486 A | 12/1995 | Lu et al. |
| 5,497,781 A | 3/1996 | Chen et al. |
| 5,638,825 A | 6/1997 | Yamazaki et al. |
| 5,702,429 A | 12/1997 | King et al. |
| 5,758,651 A | 6/1998 | Nygard et al. |
| 5,776,170 A | 7/1998 | Macdonald et al. |
| 5,785,651 A | 7/1998 | Kuhn et al. |
| 5,792,212 A | 8/1998 | Weijand et al. |
| 5,814,092 A | 9/1998 | King |
| 5,895,416 A | 4/1999 | Barreras et al. |
| 5,913,882 A | 6/1999 | King |
| 5,999,848 A | 12/1999 | Gord et al. |
| 6,020,857 A | 2/2000 | Podger |
| 6,027,456 A | 2/2000 | Feler et al. |
| 6,038,480 A | 3/2000 | Hrdlicka et al. |
| 6,066,163 A | 5/2000 | John |
| 6,114,164 A | 9/2000 | Dennis et al. |
| 6,144,881 A | 11/2000 | Hemming et al. |
| 6,157,861 A | 12/2000 | Faltys et al. |
| 6,212,431 B1 | 4/2001 | Hahn et al. |
| 6,246,912 B1 | 6/2001 | Sluijter et al. |
| 6,381,496 B1 | 4/2002 | Meadows et al. |
| 6,449,512 B1 | 9/2002 | Boveja |
| 6,463,328 B1 | 10/2002 | John |
| 6,473,649 B1 | 10/2002 | Gryzwa et al. |
| 6,473,653 B1 | 10/2002 | Schallhorn et al. |
| 6,493,576 B1 | 12/2002 | Dankwart-Eder |
| 6,516,227 B1 | 2/2003 | Meadows et al. |
| 6,522,932 B1 | 2/2003 | Kuzma |
| 6,600,955 B1 | 7/2003 | Zierhofer et al. |
| 6,658,293 B2 | 12/2003 | Vonk et al. |
| 6,675,046 B2 | 1/2004 | Holsheimer |
| 6,782,292 B2 | 8/2004 | Whitehurst |
| 6,895,280 B2 | 5/2005 | Meadows et al. |
| 6,898,582 B2 | 5/2005 | Lange et al. |
| 6,909,917 B2 | 6/2005 | Woods et al. |
| 7,089,059 B1 | 8/2006 | Pless |
| 7,171,261 B1 | 1/2007 | Litvak et al. |
| 7,177,675 B2 | 2/2007 | Suffin et al. |
| 7,206,640 B1 | 4/2007 | Overstreet |
| 7,231,254 B2 | 6/2007 | DiLorenzo et al. |
| 7,286,876 B2 | 10/2007 | Yonce et al. |
| 7,412,287 B2 | 8/2008 | Yonce et al. |
| 7,450,992 B1 | 11/2008 | Cameron |
| 7,634,315 B2 | 12/2009 | Cholette |
| 7,734,340 B2 | 6/2010 | De Ridder |
| 7,742,810 B2 | 6/2010 | Moffitt |
| 7,792,584 B2 | 9/2010 | Van Oort et al. |
| 7,818,052 B2 | 10/2010 | Litvak et al. |
| 7,831,305 B2 | 11/2010 | Gliner |
| 7,835,804 B2 | 11/2010 | Fridman et al. |
| 7,890,182 B2 | 2/2011 | Parramon et al. |
| 7,894,905 B2 | 2/2011 | Pless et al. |
| 8,190,251 B2 | 5/2012 | Molnar et al. |
| 8,224,459 B1 | 7/2012 | Pianca et al. |
| 8,239,031 B2 | 8/2012 | Fried et al. |
| 8,249,698 B2 | 8/2012 | Mugler et al. |
| 8,359,102 B2 | 1/2013 | Thacker et al. |
| 8,417,342 B1 | 4/2013 | Abell |
| 8,454,529 B2 | 6/2013 | Daly et al. |
| 8,494,645 B2 | 7/2013 | Spitzer et al. |
| 8,515,545 B2 | 8/2013 | Trier |
| 8,588,929 B2 | 11/2013 | Davis et al. |
| 8,670,830 B2 | 3/2014 | Carlson et al. |
| 8,886,323 B2 | 11/2014 | Wu et al. |
| 9,044,155 B2 | 6/2015 | Strahl |
| 9,155,892 B2 | 10/2015 | Parker et al. |
| 9,302,112 B2 | 4/2016 | Bornzin et al. |
| 9,381,356 B2 | 7/2016 | Parker et al. |
| 9,386,934 B2 | 7/2016 | Parker et al. |
| 9,872,990 B2 | 1/2018 | Parker et al. |
| 9,974,455 B2 | 5/2018 | Parker et al. |
| 10,206,596 B2 | 2/2019 | Single et al. |
| 10,278,600 B2 | 5/2019 | Parker et al. |
| 10,368,762 B2 | 8/2019 | Single |
| 10,426,409 B2 | 10/2019 | Single |
| 10,500,399 B2 | 12/2019 | Single |
| 10,568,559 B2 | 2/2020 | Parker et al. |
| 10,588,524 B2 | 3/2020 | Single et al. |
| 10,588,698 B2 | 3/2020 | Parker et al. |
| 10,632,307 B2 | 4/2020 | Parker |
| 10,842,996 B2 | 11/2020 | Baru et al. |
| 10,894,158 B2 | 1/2021 | Parker |
| 10,918,872 B2 | 2/2021 | Parker et al. |
| 11,006,846 B2 | 5/2021 | Parker et al. |
| 11,006,857 B2 | 5/2021 | Parker |
| 11,045,129 B2 | 6/2021 | Parker et al. |
| 2002/0055688 A1 | 5/2002 | Katims |
| 2002/0099419 A1 | 7/2002 | Ayal et al. |
| 2002/0193670 A1 | 12/2002 | Garfield et al. |
| 2003/0032889 A1 | 2/2003 | Wells |
| 2003/0045909 A1 | 3/2003 | Gross et al. |
| 2003/0139781 A1 | 7/2003 | Bradley et al. |
| 2003/0153959 A1 | 8/2003 | Thacker et al. |
| 2003/0195580 A1 | 10/2003 | Bradley et al. |
| 2004/0088017 A1 | 5/2004 | Sharma et al. |
| 2004/0122482 A1 | 6/2004 | Tung et al. |
| 2004/0158298 A1 | 8/2004 | Gliner |
| 2004/0225211 A1 | 11/2004 | Gozani et al. |
| 2004/0254494 A1 | 12/2004 | Spokoyny et al. |

(56) References Cited

U.S. PATENT DOCUMENTS

| | | |
|---|---|---|
| 2005/0010265 A1 | 1/2005 | Baru Fassio |
| 2005/0017190 A1 | 1/2005 | Eversmann et al. |
| 2005/0021104 A1 | 1/2005 | DiLorenzo |
| 2005/0065427 A1 | 3/2005 | Magill |
| 2005/0070982 A1 | 3/2005 | Heruth et al. |
| 2005/0075683 A1 | 4/2005 | Miesel et al. |
| 2005/0101878 A1 | 5/2005 | Daly et al. |
| 2005/0113877 A1 | 5/2005 | Giardiello et al. |
| 2005/0137670 A1 | 6/2005 | Christopherson et al. |
| 2005/0149154 A1 | 7/2005 | Cohen |
| 2005/0192567 A1 | 9/2005 | Katims |
| 2005/0203600 A1 | 9/2005 | Wallace |
| 2005/0209655 A1 | 9/2005 | Bradley et al. |
| 2005/0282149 A1 | 12/2005 | Kovacs et al. |
| 2006/0009820 A1 | 1/2006 | Royle et al. |
| 2006/0020291 A1 | 1/2006 | Gozani |
| 2006/0135998 A1 | 6/2006 | Libbus et al. |
| 2006/0195159 A1 | 8/2006 | Bradley et al. |
| 2006/0212089 A1 | 9/2006 | Tass |
| 2006/0217782 A1 | 9/2006 | Boveja et al. |
| 2006/0264752 A1 | 11/2006 | Rubinsky et al. |
| 2006/0287609 A1 | 12/2006 | Litvak et al. |
| 2007/0021800 A1 | 1/2007 | Bradley et al. |
| 2007/0073354 A1 | 3/2007 | Knudson et al. |
| 2007/0100378 A1 | 5/2007 | Maschino |
| 2007/0178579 A1 | 8/2007 | Ross et al. |
| 2007/0185409 A1 | 8/2007 | Wu et al. |
| 2007/0208394 A1 | 9/2007 | King et al. |
| 2007/0225765 A1 | 9/2007 | King |
| 2007/0225767 A1 | 9/2007 | Daly et al. |
| 2007/0244410 A1 | 10/2007 | Fridman et al. |
| 2007/0250120 A1 | 10/2007 | Flach et al. |
| 2007/0255372 A1 | 11/2007 | Metzler et al. |
| 2007/0282217 A1 | 12/2007 | McGinnis et al. |
| 2007/0287931 A1 | 12/2007 | Dilorenzo |
| 2008/0021292 A1 | 1/2008 | Stypulkowski |
| 2008/0051647 A1 | 2/2008 | Wu et al. |
| 2008/0064947 A1 | 3/2008 | Heruth et al. |
| 2008/0077191 A1 | 3/2008 | Morrell |
| 2008/0097529 A1 | 4/2008 | Parramon et al. |
| 2008/0132964 A1 | 6/2008 | Cohen et al. |
| 2008/0147155 A1 | 6/2008 | Swoyer |
| 2008/0183076 A1 | 7/2008 | Witte et al. |
| 2008/0208304 A1 | 8/2008 | Zdravkovic et al. |
| 2008/0234780 A1 | 9/2008 | Smith et al. |
| 2008/0275527 A1 | 11/2008 | Greenberg et al. |
| 2008/0294221 A1 | 11/2008 | Kilgore |
| 2008/0300655 A1 | 12/2008 | Cholette |
| 2008/0319508 A1 | 12/2008 | Botros et al. |
| 2009/0033486 A1 | 2/2009 | Costantino et al. |
| 2009/0058635 A1 | 3/2009 | Lalonde et al. |
| 2009/0082691 A1 | 3/2009 | Denison et al. |
| 2009/0149912 A1 | 6/2009 | Dacey, Jr. et al. |
| 2009/0157155 A1 | 6/2009 | Bradley |
| 2009/0270957 A1 | 10/2009 | Pianca |
| 2009/0287277 A1 | 11/2009 | Conn et al. |
| 2009/0299214 A1 | 12/2009 | Wu et al. |
| 2009/0306491 A1 | 12/2009 | Haggers |
| 2010/0010388 A1 | 1/2010 | Panken et al. |
| 2010/0057159 A1 | 3/2010 | Lozano |
| 2010/0058126 A1 | 3/2010 | Chang et al. |
| 2010/0069835 A1 | 3/2010 | Parker |
| 2010/0069996 A1 | 3/2010 | Strahl |
| 2010/0070007 A1 | 3/2010 | Parker |
| 2010/0070008 A1 | 3/2010 | Parker |
| 2010/0100153 A1 | 4/2010 | Carlson et al. |
| 2010/0106231 A1 | 4/2010 | Torgerson |
| 2010/0114237 A1 | 5/2010 | Giftakis et al. |
| 2010/0114258 A1 | 5/2010 | Donofrio et al. |
| 2010/0125313 A1 | 5/2010 | Lee et al. |
| 2010/0125314 A1 | 5/2010 | Bradley et al. |
| 2010/0145222 A1 | 6/2010 | Brunnett et al. |
| 2010/0152808 A1 | 6/2010 | Boggs, II |
| 2010/0179626 A1 | 7/2010 | Pilarski |
| 2010/0191307 A1 | 7/2010 | Fang et al. |
| 2010/0204748 A1 | 8/2010 | Lozano et al. |
| 2010/0222844 A1 | 9/2010 | Troosters et al. |
| 2010/0222858 A1 | 9/2010 | Meloy |
| 2010/0249643 A1 | 9/2010 | Gozani et al. |
| 2010/0249867 A1 | 9/2010 | Wanasek |
| 2010/0258342 A1 | 10/2010 | Parker |
| 2010/0262208 A1 | 10/2010 | Parker |
| 2010/0262214 A1 | 10/2010 | Robinson |
| 2010/0280570 A1 | 11/2010 | Sturm et al. |
| 2010/0286748 A1 | 11/2010 | Midani et al. |
| 2010/0331604 A1 | 12/2010 | Okamoto et al. |
| 2010/0331926 A1 | 12/2010 | Lee et al. |
| 2011/0004207 A1 | 1/2011 | Wallace et al. |
| 2011/0021943 A1 | 1/2011 | Lacour et al. |
| 2011/0028859 A1 | 2/2011 | Chian |
| 2011/0040546 A1 | 2/2011 | Gerber et al. |
| 2011/0077712 A1 | 3/2011 | Killian |
| 2011/0087085 A1 | 4/2011 | Tsampazis et al. |
| 2011/0093042 A1 | 4/2011 | Torgerson et al. |
| 2011/0106100 A1 | 5/2011 | Bischoff |
| 2011/0184488 A1 | 7/2011 | De Ridder et al. |
| 2011/0204811 A1 | 8/2011 | Pollmann-retsch |
| 2011/0224665 A1 | 9/2011 | Crosby et al. |
| 2011/0224749 A1 | 9/2011 | Ben-David et al. |
| 2011/0264165 A1 | 10/2011 | Molnar et al. |
| 2011/0270343 A1 | 11/2011 | Buschman et al. |
| 2011/0307030 A1 | 12/2011 | John |
| 2011/0313310 A1 | 12/2011 | Tomita |
| 2011/0313483 A1 | 12/2011 | Hincapie et al. |
| 2012/0029377 A1 | 2/2012 | Polak |
| 2012/0059275 A1 | 3/2012 | Fagin et al. |
| 2012/0101552 A1 | 4/2012 | Lazarewicz et al. |
| 2012/0101826 A1 | 4/2012 | Visser et al. |
| 2012/0109004 A1 | 5/2012 | Cadwell |
| 2012/0109236 A1 | 5/2012 | Jacobson et al. |
| 2012/0155183 A1 | 6/2012 | Aritome |
| 2012/0185020 A1* | 7/2012 | Simon ............... A61N 1/36014 607/74 |
| 2012/0253423 A1 | 10/2012 | Youn et al. |
| 2012/0277621 A1 | 11/2012 | Gerber et al. |
| 2012/0277823 A1 | 11/2012 | Gerber et al. |
| 2012/0310301 A1 | 12/2012 | Bennett et al. |
| 2013/0041449 A1 | 2/2013 | Cela et al. |
| 2013/0053722 A1 | 2/2013 | Carlson et al. |
| 2013/0060302 A1 | 3/2013 | Polefko et al. |
| 2013/0172774 A1 | 7/2013 | Crowder et al. |
| 2013/0289661 A1 | 10/2013 | Griffith et al. |
| 2013/0289683 A1 | 10/2013 | Parker et al. |
| 2014/0066803 A1 | 3/2014 | Choi |
| 2014/0142447 A1 | 5/2014 | Takahashi et al. |
| 2014/0194771 A1 | 7/2014 | Parker et al. |
| 2014/0194772 A1 | 7/2014 | Single et al. |
| 2014/0236042 A1 | 8/2014 | Parker et al. |
| 2014/0236257 A1 | 8/2014 | Parker et al. |
| 2014/0243926 A1 | 8/2014 | Carcieri |
| 2014/0243931 A1 | 8/2014 | Parker et al. |
| 2014/0249396 A1 | 9/2014 | Shacham-diamand et al. |
| 2014/0276195 A1 | 9/2014 | Papay et al. |
| 2014/0277250 A1 | 9/2014 | Su et al. |
| 2014/0277267 A1 | 9/2014 | Vansickle et al. |
| 2014/0288551 A1 | 9/2014 | Bharmi et al. |
| 2014/0288577 A1 | 9/2014 | Robinson et al. |
| 2014/0296737 A1 | 10/2014 | Parker et al. |
| 2014/0324118 A1 | 10/2014 | Simon et al. |
| 2014/0350634 A1 | 11/2014 | Grill et al. |
| 2014/0358024 A1 | 12/2014 | Nelson et al. |
| 2015/0018699 A1 | 1/2015 | Zeng et al. |
| 2015/0025597 A1 | 1/2015 | Surth et al. |
| 2015/0126839 A1 | 5/2015 | Li et al. |
| 2015/0148869 A1 | 5/2015 | Dorvall, II et al. |
| 2015/0164354 A1 | 6/2015 | Parker et al. |
| 2015/0174396 A1 | 6/2015 | Fisher et al. |
| 2015/0238104 A1 | 8/2015 | Tass |
| 2015/0238304 A1 | 8/2015 | Lamraoui |
| 2015/0282725 A1 | 10/2015 | Single |
| 2015/0313487 A1 | 11/2015 | Single |
| 2015/0360031 A1 | 12/2015 | Bornzin et al. |
| 2015/0374999 A1 | 12/2015 | Parker |
| 2016/0082265 A1 | 3/2016 | Moffitt et al. |

(56) References Cited

U.S. PATENT DOCUMENTS

| | | | |
|---|---|---|---|
| 2016/0082268 A1* | 3/2016 | Hershey | A61N 1/36189 607/46 |
| 2016/0101289 A1 | 4/2016 | Stolen et al. | |
| 2016/0106980 A1 | 4/2016 | Sürth et al. | |
| 2016/0121124 A1* | 5/2016 | Johanek | A61N 1/37264 607/62 |
| 2016/0129272 A1 | 5/2016 | Hou et al. | |
| 2016/0144189 A1 | 5/2016 | Bakker et al. | |
| 2016/0166164 A1 | 6/2016 | Obradovic et al. | |
| 2016/0175594 A1 | 6/2016 | Min et al. | |
| 2016/0287126 A1 | 10/2016 | Parker et al. | |
| 2016/0287182 A1 | 10/2016 | Single | |
| 2016/0367808 A9* | 12/2016 | Simon | A61N 1/36025 |
| 2017/0001017 A9 | 1/2017 | Parker et al. | |
| 2017/0049345 A1 | 2/2017 | Single | |
| 2017/0071490 A1 | 3/2017 | Parker et al. | |
| 2017/0135624 A1 | 5/2017 | Parker | |
| 2017/0173335 A1 | 6/2017 | Min et al. | |
| 2017/0173341 A1 | 6/2017 | Johanek et al. | |
| 2017/0216587 A1 | 8/2017 | Parker | |
| 2017/0361101 A1 | 12/2017 | Single | |
| 2018/0071513 A1 | 3/2018 | Weiss et al. | |
| 2018/0104493 A1 | 4/2018 | Doan et al. | |
| 2018/0110987 A1 | 4/2018 | Parker | |
| 2018/0117335 A1 | 5/2018 | Parker et al. | |
| 2018/0132747 A1 | 5/2018 | Parker et al. | |
| 2018/0132760 A1 | 5/2018 | Parker | |
| 2018/0133459 A1 | 5/2018 | Parker et al. | |
| 2018/0228391 A1 | 8/2018 | Parker et al. | |
| 2018/0228547 A1 | 8/2018 | Parker | |
| 2018/0229046 A1 | 8/2018 | Parker et al. | |
| 2018/0256052 A1 | 9/2018 | Parker et al. | |
| 2019/0001139 A1 | 1/2019 | Mishra et al. | |
| 2019/0030339 A1 | 1/2019 | Baru et al. | |
| 2019/0125269 A1 | 5/2019 | Markovic et al. | |
| 2019/0216343 A1 | 7/2019 | Single et al. | |
| 2019/0239768 A1 | 8/2019 | Karantonis et al. | |
| 2019/0307341 A1 | 10/2019 | Parker et al. | |
| 2019/0357788 A1 | 11/2019 | Single | |
| 2020/0029914 A1 | 1/2020 | Single | |
| 2020/0129108 A1 | 4/2020 | Parker et al. | |
| 2020/0155240 A1 | 5/2020 | Parker et al. | |
| 2020/0215331 A1 | 7/2020 | Single | |
| 2020/0282208 A1 | 9/2020 | Parker | |
| 2021/0001133 A1 | 1/2021 | Williams et al. | |
| 2021/0016091 A1 | 1/2021 | Parker et al. | |
| 2021/0121696 A1 | 4/2021 | Parker et al. | |
| 2021/0162214 A1 | 6/2021 | Parker | |

FOREIGN PATENT DOCUMENTS

| | | |
|---|---|---|
| CN | 103654762 A | 3/2014 |
| CN | 103842022 A | 6/2014 |
| CN | 104411360 A | 3/2015 |
| EP | 0219084 | 4/1987 |
| EP | 1244496 A1 | 10/2002 |
| EP | 0998958 B1 | 8/2005 |
| EP | 2019716 A | 11/2007 |
| EP | 2243510 A2 | 10/2010 |
| EP | 2443995 A2 | 4/2012 |
| EP | 2520327 A2 | 11/2012 |
| EP | 2707095 A1 | 3/2014 |
| EP | 3229893 A1 | 10/2017 |
| JP | 2006504494 A | 2/2006 |
| JP | 2009512505 A | 3/2009 |
| JP | 2012524629 | 10/2012 |
| JP | 2013500779 A | 1/2013 |
| JP | 2013527784 A | 7/2013 |
| JP | 2013536044 A | 9/2013 |
| JP | 2014522261 A | 9/2014 |
| JP | 2014523261 A | 9/2014 |
| WO | 1983003191 A | 9/1983 |
| WO | 1993001863 A1 | 2/1993 |
| WO | 1996012383 A1 | 4/1996 |
| WO | 2000002623 A1 | 1/2000 |
| WO | 2002036003 A1 | 11/2001 |
| WO | 2002038031 | 5/2002 |
| WO | 2002049500 A2 | 6/2002 |
| WO | 2003028521 A2 | 4/2003 |
| WO | 2003043690 | 5/2003 |
| WO | 2003103484 | 12/2003 |
| WO | 2004021885 A1 | 3/2004 |
| WO | 2004103455 | 12/2004 |
| WO | 2005032656 A1 | 4/2005 |
| WO | 2005105202 A1 | 11/2005 |
| WO | 2005122887 A2 | 12/2005 |
| WO | 2006091636 A2 | 8/2006 |
| WO | 2007050657 A1 | 5/2007 |
| WO | 2007064936 A1 | 6/2007 |
| WO | 2007127926 A2 | 11/2007 |
| WO | 2007130170 A1 | 11/2007 |
| WO | 2008004204 A1 | 1/2008 |
| WO | 2008049199 A1 | 5/2008 |
| WO | 2009002072 A2 | 12/2008 |
| WO | 2009002579 A1 | 12/2008 |
| WO | 2009010870 A2 | 1/2009 |
| WO | 2009130515 A2 | 10/2009 |
| WO | 2009146427 A1 | 12/2009 |
| WO | 2010013170 A1 | 2/2010 |
| WO | 2010044989 A2 | 4/2010 |
| WO | 2010051392 A1 | 5/2010 |
| WO | 2010051406 A1 | 5/2010 |
| WO | 2010057046 A2 | 5/2010 |
| WO | 2010124139 A1 | 10/2010 |
| WO | 2010138915 A1 | 12/2010 |
| WO | 2011011327 A1 | 1/2011 |
| WO | 2011014570 A1 | 2/2011 |
| WO | 2011066477 A1 | 6/2011 |
| WO | 2011066478 A1 | 6/2011 |
| WO | 2011112843 A1 | 9/2011 |
| WO | 2011119251 A2 | 9/2011 |
| WO | 2011159545 A2 | 12/2011 |
| WO | 2012027252 A2 | 3/2012 |
| WO | 2012027791 A1 | 3/2012 |
| WO | 2012155183 A1 | 11/2012 |
| WO | 2012155184 A1 | 11/2012 |
| WO | 2012155185 A1 | 11/2012 |
| WO | 2012155187 A1 | 11/2012 |
| WO | 2012155188 A1 | 11/2012 |
| WO | 2012155189 A1 | 11/2012 |
| WO | 2012155190 A1 | 11/2012 |
| WO | 2012162349 A1 | 11/2012 |
| WO | 2013063111 A1 | 5/2013 |
| WO | 2013075171 A1 | 5/2013 |
| WO | 2014071445 A1 | 5/2014 |
| WO | 2014071446 A1 | 5/2014 |
| WO | 2014143577 A1 | 9/2014 |
| WO | 2014150001 A1 | 9/2014 |
| WO | 2015070281 A1 | 5/2015 |
| WO | 2015074121 A1 | 5/2015 |
| WO | 2015109239 A1 | 7/2015 |
| WO | 2015143509 A1 | 10/2015 |
| WO | 2015168735 A1 | 11/2015 |
| WO | 2016011512 | 1/2016 |
| WO | 2016048974 A1 | 3/2016 |
| WO | 2016059556 A1 | 4/2016 |
| WO | 2016077882 A1 | 5/2016 |
| WO | 2016090420 A1 | 6/2016 |
| WO | 2016090436 A1 | 6/2016 |
| WO | 2016115596 A1 | 7/2016 |
| WO | 2016161484 A1 | 10/2016 |
| WO | 2016168798 A1 | 10/2016 |
| WO | 2016191807 A1 | 12/2016 |
| WO | 2016191808 A1 | 12/2016 |
| WO | 2016191815 A1 | 12/2016 |
| WO | 2017173493 A1 | 10/2017 |
| WO | 2017210352 A1 | 12/2017 |
| WO | 2017219096 A1 | 12/2017 |
| WO | 2018119220 A1 | 6/2018 |
| WO | 2018160992 A1 | 9/2018 |
| WO | 2019178634 A1 | 9/2019 |
| WO | 2019204884 A1 | 10/2019 |
| WO | 2019231796 A1 | 12/2019 |

(56) References Cited

FOREIGN PATENT DOCUMENTS

| WO | 2020082118 A1 | 4/2020 |
|----|---------------|--------|
| WO | 2020082126 A1 | 4/2020 |
| WO | 2020082128 A1 | 4/2020 |
| WO | 2020087123 A1 | 5/2020 |
| WO | 2020087135 A1 | 5/2020 |
| WO | 2020124135 A1 | 6/2020 |

OTHER PUBLICATIONS

Extended European Search Report for European Application No. 16802238.2, Search completed Oct. 17, 2018, dated Oct. 24, 2018, 8 Pgs.
International Preliminary Report for International Application No. PCT/AU2017/050647, dated Dec. 25, 2018, 8 pgs.
International Search Report and Written Opinion for International Application No. PCT/AU2017/050647, Search completed Sep. 29, 2017, dated Sep. 29, 2017, 13 Pgs.
Bahmer et al., "Application of triphasic pulses with adjustable phase amplitude ratio (PAR) for cochlear ECAP recording: I. Amplitude growth functions", Journal of Neuroscience Methods, Clinical Neuroscience, 2012, vol. 205, pp. 202-211.
Bahmer et al., "Effects of electrical pulse polarity shape on intra cochlear neural responses in humans: Triphasic pulses with cathodic second phase", Hearing Research, 2013, vol. 306, pp. 123-130.
Gnadt et al., "Spectral Cancellation of Microstimulation Artifact for Simultaneous Neural Recording In Situ", IEEE Transactions on Biomedical Engineering, Oct. 2003, Date of Publication: Sep. 23, 2003, vol. 50, No. 10, pp. 1129-1135, DOI: 10.1109/TBME.2003. 816077.
Jeffrey et al., "A reliable method for intracranial electrode implantation and chronic electrical stimulation in the mouse brain", BMC Neuroscience. Biomed Central. London. GB. vol. 14. No. 1. Aug. 6, 2013 (Aug. 6, 2013) • p. 82.
Tronnier et al., "Magnetic Resonance Imaging with Implanted Neurostimulators: An In Vitro and In Vivo Study", Jan. 1999, Neurosurgery, vol. 44(1), p. 118-125 (Year: 1999).
International Preliminary Report for International Application No. PCT/AU2017/050296, dated Oct. 9, 2018, 7 Pgs.
European Search Report for European Application 12785619.3 Search Completed Oct. 13, 2014, dated Oct. 23, 2014, 7 pgs.
European Search Report for European Application 12785669.8 Search Completed Sep. 22, 2014, dated Sep. 29, 2014, 5 pgs.
European Search Report for European Application No. 15861444.6, Search completed Jul. 13, 2018, dated Jul. 23, 2018, 8 pgs.
Extended European Search Report for EP Application 12785483.4 completed Sep. 16, 2014, 7 pgs.
Extended European Search Report for European Application No. 11820923.8, report completed Dec. 9, 2013, report dated Dec. 17, 2013, 6 pgs.
Extended European Search Report for European Application No. 13852669.4, Search completed Jun. 8, 2016, dated Jun. 22, 2016, 9 pgs.
Extended European Search Report for European Application No. 14861553.7, Search completed Jun. 8, 2017, dated Jun. 19, 2017, 8 pgs.
Extended European Search Report for European Application No. 14863597.2, Search completed Jun. 6, 2017, dated Jun. 13, 2017, 9 pgs.
Extended European Search Report for European Application No. 15768956.3, Search completed Oct. 3, 2017, dated Oct. 10, 2017, 8 pgs.
Extended European Search Report for European Application No. 16739680.3, Search completed Jun. 1, 2018, dated Jun. 12, 2018, 9 pgs.
Extended European Search Report for European Application No. 13853514.1, Search completed Jun. 8, 2016, dated Jun. 15, 2016, 7 pgs.
International Preliminary Report on Patentability for International Application No. PCT/AU2011/001127, Report dated Mar. 5, 2013, 9 pgs.
International Preliminary Report on Patentability for International Application No. PCT/AU2012/000511, Report dated Nov. 19, 2013, 6 pgs.
International Preliminary Report on Patentability for International Application No. PCT/AU2012/000512, Report dated Nov. 19, 2013, 8 pgs.
International Preliminary Report on Patentability for International Application No. PCT/AU2012/000513, Report dated Nov. 19, 2013, 11 pgs.
International Preliminary Report on Patentability for International Application No. PCT/AU2012/000515, Report dated Nov. 19, 2013, 5 pgs.
International Preliminary Report on Patentability for International Application No. PCT/AU2012/000516, Report dated Nov. 19, 2013, 9 pgs.
International Preliminary Report on Patentability for International Application No. PCT/AU2012/000517, Report dated Nov. 19, 2013, 6 pgs.
International Preliminary Report on Patentability for International Application No. PCT/AU2012/000518, Report dated Nov. 19, 2013, 11 pgs.
International Preliminary Report on Patentability for International Application No. PCT/AU2012/001441, Report dated May 27, 2014, 10 pgs.
International Preliminary Report on Patentability for International Application No. PCT/AU2013/001279, Report dated May 12, 2015, 6 pgs.
International Preliminary Report on Patentability for International Application No. PCT/AU2013/001280, Report dated May 12, 2015, 6 pgs.
International Preliminary Report on Patentability for International Application No. PCT/AU2014/001049, Report dated May 17, 2016, 5 pgs.
International Preliminary Report on Patentability for International Application No. PCT/AU2014/050369, Report dated May 24, 2016, 8 pgs.
International Preliminary Report on Patentability for International Application No. PCT/AU2015/050135, Report dated Oct. 4, 2016, 13 pgs.
International Preliminary Report on Patentability for International Application No. PCT/AU2015/050215, Report dated Nov. 8, 2016, 4 pgs.
International Preliminary Report on Patentability for International Application No. PCT/AU2015/050422, Report dated Jan. 31, 2017, 8 pgs.
International Preliminary Report on Patentability for International Application No. PCT/AU2015/050724, Report dated May 23, 2017, 5 pgs.
International Preliminary Report on Patentability for International Application No. PCT/AU2015/050753, Report dated Jun. 13, 2017, 7 pgs.
International Preliminary Report on Patentability for International Application No. PCT/AU2015/050787, Report dated Jun. 13, 2017, 6 pgs.
International Preliminary Report on Patentability for International Application No. PCT/AU2016/050019, Report dated Jul. 25, 2017, 9 pgs.
International Preliminary Report on Patentability for International Application No. PCT/AU2016/050263, Report dated Oct. 10, 2017, 9 pgs.
International Search Report & Written Opinion for International Application No. PCT/AU2013/001280, Search Completed Jan. 16, 2014, dated Jan. 16, 2014, 8 pgs.
International Search Report & Written Opinion for International Application PCT/AU2013/001279, Search Completed Jan. 9, 2014, dated Jan. 9, 2014, 9 pgs.
International Search Report and Written Opinion for International Application No. PCT/AU2011/001127, date completed Nov. 11, 2011, dated Nov. 15, 2011, 13 pgs.

(56) References Cited

OTHER PUBLICATIONS

International Search Report and Written Opinion for International Application No. PCT/AU2012/001441, International Filing Date Nov. 23, 2012, Search Completed Feb. 26, 2013, dated Feb. 26, 2013, 14 pgs.
International Search Report and Written Opinion for International Application No. PCT/AU2014/001049, Search completed Feb. 10, 2015, dated Feb. 10, 2015, 8 pgs.
International Search Report and Written Opinion for International Application No. PCT/AU2014/050369, Search completed Feb. 20, 2015, dated Feb. 20, 2015, 14 pgs.
International Search Report and Written Opinion for International Application No. PCT/AU2015/050135, Search completed Jun. 30, 2015, dated Jun. 30, 2015, 26 pgs.
Fagius, J. et al., "Sympathetic Reflex Latencies and Conduction Velocities in Normal Man", Journal of Neurological Sciences, 1980. vol. 47, pp. 433-448.
Falowski et al., "Spinal Cord Stimulation: an update", Neurotherapeutics: The Journal of the American Society for Experimental NeuroTherapeutics 5, No. 1, Jan. 2008, pp. 86-99.
Fisher, "F-Waves—Physiology and Clinical Uses", TheScientificWorldJournal, (2007) 7, pp. 144-160.
Franke, Felix et al., "An Online Spike Detection and Spike Classification Algorithm Capable of Instantaneous Resolution of Overlapping Spikes", Journal of Computational Neuroscience, 2010, vol. 29, No. 1-2, pp. 127-148.
French et al., "Information transmission at 500 bits/s by action potentials in a mechanosensory neuron of the cockroach", Neuroscience Letters, vol. 243, No. 1-3, Feb. 1, 1998, pp. 113-116.
Fuentes et al., "Spinal Cord Stimulation Restores Locomotion in Animal Models of Parkinson's Disease", Science, vol. 323, No. 5921, Mar. 20, 2009, pp. 1578-1582.
Gad et al., "Development of a multi-electrode array for spinal cord epidural stimulation to facilitate stepping and standing after a complete spinal cord injury in adult rats", Journal of NeuroEngineering and Rehabilitation 2013, 10:2, 18 pgs.
George et al., "Vagus nerve stimulation: a new tool for brain research and therapy", Biological Psychiatry 47, No. 4, Feb. 15, 2000, pp. 287-295.
Goodall, E. V., "Modeling Study of Activation and Propagation delays During Stimulation of Peripheral Nerve Fibres with a Tripolar Cuff Electrode", IEEE Transactions on Rehabilitation Engineering, vol. 3, No. 3, Sep. 1995, pp. 272-282.
Gorman et al., "ECAP Mapping of the Spinal Cord: Influence of Electrode Position on Aβ Recruitment", (2012), In 16th Annual Meeting. Presented at the North American Neuromodulation Society, Las Vegas, NV.
Gorman et al., "Neural Recordings For Feedback Control Of Spinal Cord Stimulation: Reduction Of Paresthesia Variability.", 2013, In International Neuromodulation Society 11th World Congress. Presented at the International Neuromodulation Society 11th World Congress, Berlin, Germany.
Hallstrom et al., "Distribution of lumbar spinal evoked potentials and their correlation with stimulation-induced paresthesiae", (1991), Electroencephalography and clinical neurophysiology 80:126-139.
Harper, A. et al., "Conduction Velocity is Related to Morphological Cell Type in Rat Dorsal Root Ganglion Neurones", J. Physiol, (1985), 359, pp. 31-46.
He et al., "Perception threshold and electrode position for spinal cord stimulation", Pain, 59 (1994) 55-63 pages.
Herreras, "Local Field Potentials: Myths and Misunderstandings", Frontiers in Neural Circuits, Dec. 15, 2016, vol. 10, Article 1101, 16 pgs.
Holsheimer et al., "Optimum Electrode Geometry for Spinal Cord Stimulation: the Narrow Bipole and Tripole", Medical and Biological Engineering and Computing, 35, No. 5, 1997, pp. 493-497.
Holsheimer et al., "Significance of the Spinal Cord Position in Spinal Cord Stimulation", Acta Neurochir (1995) [Suppl] 64: 119-124 pages.
Holsheimer et al., "Spinal Geometry and Paresthesia Coverage in Spinal Cord Stimulation", (1998 paper) 8 pages.
Huff, Terry B. et al., "Real-Time CARS Imaging Reveals a Calpain-Dependent Pathway for Paranodal Myelin Retraction during High-Frequency Stimulation", PLoS ONE vol. 6, Issue 3 (Mar. 3, 2011): e17176, 11 pgs.
Kent et al., "Instrumentation to Record Evoked Potentials for Closed-Loop Control of Deep Brain Stimulation", Conf. Proc. IEEE Eng. Med Biol. Sol, Aug. 2012, 10 pgs.
Kent, AR et al., "Recording evoked potentials during deep brain stimulation: development and validation of instrumentation to suppress the stimulus artefact", J Neural Eng. Jun. 2012; 9 (3):036004, Apr. 18, 2012. doi: 10.1088/1741-2560/9/3/036004.
Kim et al., "A Wavelet-Based Method for Action Potential Detection From Extracellular Neural Signal Recording With Low Signal-to-Noise Ratio", IEEE Transactions On Biomedical Engineering, vol. 50. No. 8, Aug. 2003.
Kim et al., "Cell Type-specific Changes of the Membrane Properties of Peripherally-axotomized Dorsal Root Ganglion Neurons in a Rat Model of Neuropathic Pain", Neuroscience 86, No. 1 (May 21, 1998): pp. 301-309, doi:10.1016/S0306-4522(98)00022-0.
Krames et al., "Neuromodulation", 1st Edition, Academic Press, 2009, p. 540-541.
Krarup, Christian, "Compound sensory action potential in normal and pathological human nerves", Muscle & nerve, vol. 29, No. 4 (2004), pp. 465-483.
Krishnan et al., "Excitability Differences in Lower-Limb Motor Axons During and After Ischemia", Muscle & Nerve, vol. 31, No. 2 (2005), pp. 205-213.
Kumar et al., "Deep Brain Stimulation for Intractable Pain: a 15-year Experience", Neurosurgery, Issue 40, No. 4, Apr. 1997, pp. 736-747.
Kumar et al., "Double-blind evaluation of subthalamic nucleus deep brain stimulation in advanced Parkinson's disease", by the American Academy of Neurology, 51, No. 3, Sep. 1, 1998, pp. 850-855.
Kumar et al., "Globus Pallidus Deep Brain Stimulation for Generalized Dystonia: Clinical and PET Investigation", Neurology, 53, No. 4, 1999, pp. 871-874.
Laird et al., "A Model of Evoked Potentials in Spinal Cord Stimulation", IEEE Engineering in Medicine & Biology Society, 35th Annual Conference. Osaka, Japan: Jul. 3-7, 2013, pp. 6555-6558.
Lempka, Scott, "The Electrode-Tissue Interface During Recording and Stimulation In The Central Nervous System", published on May 2010.
Levy et al., "Incidence and Avoidance of Neurologic Complications with Paddle Type Spinal Cord Stimulation Leads", Neuromodulation 14(15), Sep. 2011, pp. 412-422.
Li, S et al., "Resonant antidromic cortical circuit activation as a consequence of high-frequency subthalamic deep-brain stimulation", J Neurophysiol. Dec. 2007; 98(6): 3525-37. First published Oct. 10, 2007. doi:10.1152/jn.00808.2007.
Ma et al., "Similar Electrophysiological Changes in Axotomized and Neighboring Intact Dorsal Root Ganglion Neurons", Journal of Neurophysiology 89, No. 3 (Mar. 1, 2003): 1588-1602, doi:10.1152/jn.00855.2002.
Macefield, "Spontaneous and Evoked Ectopic Discharges Recorded from Single Human Axons", Muscle & Nerve 21, No. 4, Apr. 1998, pp. 461-468.
Mahnam et al., "Measurement of the current-distance relationship using a novel refractory interaction technique", J. Neural Eng. 6(2): 036005, published May 20, 2009, 22 pgs.
Markandey, Vishal, "ECG Implementation on the TMS320C5515 DSP Medical Development Kit (MDK)", Texas Instruments Application Report Jun. 2010, 35 pgs.
Massachusetts Institute of Techn, "The Compound Action Potential of the Frog Sciatic Nerve", Quantitative Physiology: Cells and Tissues. Fall, 1999, Retrieved from http://umech.mit.edu/freeman/6.021J/2001/lab.pdf on May 22, 2012.
Matzner et al., "Na+ Conductance and the Threshold for Repetitive Neuronal Firing", Brain Research 597, No. 1 (Nov. 27, 1992): pp. 92-98, doi:10.1016/0006-8993(92)91509-D.
McGill, Kevin et al., "On the Nature and Elimination of Stimulus Artifact in Nerve Signals Evoked and Recorded Using Surface

(56) References Cited

OTHER PUBLICATIONS

Electrodes", IEEE Transactions On Biomedical Engineering, vol. BME-29, No. 2, Feb. 1982, pp. 129-137.
Melzack et al., "Pain mechanisms: a new theory", Science, New York, New York, vol. 150, No. 3699, Nov. 19, 1965, pp. 971-979.
Miles et al., "An Electrode for Prolonged Stimulation of the Brain", Proc. 8th Meeting World Soc. Stereotactic and Functional Neurosurgery, Part III, Zurich, 1981, Appl. Neurophysiol, 45, 1982, pp. 449-455.
Misawa et al., "Neuropathic Pain Is Associated with Increased Nodal Persistent Na(+) Currents in Human Diabetic Neuropathy", Journal of the Peripheral Nervous System: JPNS, 14, No. 4 (Dec. 2009): 279-284.
Nordin et al., "Ectopic Sensory Discharges and Paresthesiae in Patients with Disorders of Peripheral Nerves, Dorsal Roots and Dorsal Columns", Pain 20, No. 3 (Nov. 1984): 231-245, doi:10.1016/0304-3959(84)90013-7.
Oakley et al., "Spinal Cord Stimulation: Mechanisms of Action", Spine 27, No. 22, Nov. 15, 2002, pp. 2574-2583.
Oakley et al., "Transverse Tripolar Spinal Cord Stimulation: Results of an International Multicenter Study", Neuromodulation, vol. 9, No. 3, 2006, pp. 192-203.
Obradovic et al., "Effect of pressure on the spinal cord during spinal cord stimulation in an animal model", Poster, 18th Annual Meeting of the North American Neuromodulation Society, Dec. 11-14, 2014, Las Vegas.
Oh et al., "Long-term hardware-related complications of deep brain stimulation", Neurosurgery, vol. 50, No. 6, Jun. 2002, pp. 1268-1274, discussion pp. 1274-1276.
Olin et al., "Postural Changes in Spinal Cord Stimulation Perceptual Thresholds", Neuromodulation, vol. 1, No. 4, 1998, pp. 171-175.
Opsommer, E. et al., "Determination of Nerve Conduction Velocity of C-fibres in Humans from Thermal Thresholds to Contact Heat (Thermode) and from Evoked Brain Potentials to Radiant Heat (CO2 Laser)", Neurophysiologie Clinique 1999, vol. 29, pp. 411-422.
Orstavik, Kristin et al., "Pathological C-fibres in patients with a chronic painful condition", Brain (2003), 126, pp. 567-578.
Ouyang et al., "Compression Induces Acute Demyelination and Potassium Channel Exposure in Spinal Cord", Journal of Neurotrauma 27, No. 6, Jun. 2010, 1109-1120, doi:10.1089/neu.2010.1271.
Parker et al., "Closing the Loop in Neuromodulation Therapies: Spinal Cord Evoked Compound Action Potentials During Stimulation for Pain Management (230).", 2011, In 15th Annual Meeting, North American Neuromodulation Society (p. 48). Presented at the North American Neuromodulation Society, Las Vegas.
Parker et al., "Compound Action Potentials Recorded in the Human Spinal Cord During Neurostimulation for Pain Relief", Pain, vol. 153, 2012, pp. 593-601.
Partial European Search Report for European Application No. 16775966.1, Search completed Oct. 26, 2018, dated Nov. 6, 2018, 11 Pgs.
Parker et al., "Electrically Evoked Compound Action Potentials Recorded From the Sheep Spinal Cord", Neuromodulation, vol. 16, 2013, pp. 295-303.
Penar et al., "Cortical Evoked Potentials Used for Placement of a Laminotomy Lead Array: A Case Report", Neuromodulation: Technology at the Neural Interface, accessed Apr. 19, 2011, doi:10.1111/j.1525-1403.2011.00352.x.
Rattay, "Analysis of Models for External Stimulation of Axons", IEEE Transactions on Biomedical Engineering, vol. BME-33, No. 10, Oct. 1986, pp. 974-977.
Richter et al., "EMG and SSEP Monitoring During Cervical Spinal Cord Stimulation", Journal of Neurosurgical Review 2011, Southern Academic Press, 1(S1), 2011, pp. 61-63.
Ridder et al., "Burst Spinal Cord Stimulation for Limb and Back Pain", World Neurosurgery, 2013, 9 pgs.
Ross et al., "Improving Patient Experience with Spinal Cord Stimulation Implications of Position-Related Changes in Neurostimulation", Neuromodulation 2011; e-pub ahead of print. DOI: 10.1111/j.1525-1403.2011.00407.x 6 pages.
Roy, S. H. et al., "Effects of Electrode Location on Myoelectric Conduction Velocity and Median Frequency Estimates", J. Appl. Physiol. 61 (4), 1986, pp. 1510-1517.
Sayenko et al., "Neuromodulation of evoked muscle potentials induced by epidural spinal-cord stimulation in paralyzed individuals", Journal of Neurophysiology, vol. 111, No. 5, 2014, pp. 1088-1099, First published Dec. 11, 2013.
Schmidt et al., "Gating of tactile input from the hand", Exp Brain Res, 1990, 79, pp. 97-102.
Siegfried et al., "Bilateral Chronic Electrostimulation of Ventroposterolateral Pallidum: A New Therapeutic Approach for Alleviating all Parkinsonian Symptoms", Neurosurgery, 35, No. 6, Dec. 1994, pp. 1126-1130.
Siegfried et al., "Intracerebral Electrode Implantation System", Journal of Neurosurgery, vol. 59, No. 2, Aug. 1983, pp. 356-359.
Srinivasan, S., "Electrode/Electrolyte Interfaces: Structure and Kinetics of Charge Transfer", Fuel Cells, 2006, Chapter 2, 67 pages.
Struijk, "The Extracellular Potential of a Myelinated Nerve Fiber in an Unbounded Medium and in Nerve Cuff Models", Biophysical Journal, vol. 72, Jun. 1997, pp. 2457-2469.
Struijk et al., "Paresthesia Thresholds in Spinal Cord Stimulation: A Comparison of Theoretical Results with Clinical Data", IEEE Transactions on Rehabilitation Engineering, vol. 1, No. 2, Jun. 1993, pp. 101-108.
Struijk et al., "Excitation of Dorsal Root Fibers in Spinal Cord Stimulation: a Theoretical Study", IEEE Transactions on Biomedical Engineering, Jul. 1993, vol. 40, No. 7, pp. 632-639.
Sufka et al., "Gate Control Theory Reconsidered", Brain and Mind, 3, No. 2, 2002, pp. 277-290.
Tamura et al., "Increased Nodal Persistent Na+ Currents in Human Neuropathy and Motor Neuron Disease Estimated by Latent Addition", Clinical Neurophysiology 117, No. 11 (Nov. 2006): pp. 2451-2458, doi:10.1016/j.clinph.2006.07.309.
Tasker, "Deep Brain Stimulation is Preferable to Thalamotomy for Tremor Suppression", Surgical Neurology, 49, No. 2, 1998, pp. 145-153.
Taylor et al., "Spinal Cord Stimulation for Chronic Back and Leg Pain and Failed Back Surgery Syndrome: A Systematic Review and Analysis of Prognostic Factors", Spine, vol. 30, No. 1, 2004, pp. 152-160.
Texas Instruments, "Precision, Low Power Instrumentation Amplifiers", Texas Instruments SBOS051B Oct. 1995, Revised Feb. 2005, 20 pgs.
Tomas et al., "Dorsal Root Entry Zone (DREZ) Localization Using Direct Spinal Cord Stimulation Can Improve Results of the DREZ Thermocoagulation Procedure for Intractable Pain Relief", Pain, 2005, vol. 116, pp. 159-163.
Tscherter et al., "Spatiotemporal Characterization of Rhythmic Activity in Rat Spinal Cord Slice Cultures", European Journal of Neuroscience 14, No. 2 (2001), pp. 179-190.
Van Den Berg et al., "Nerve fiber size-related block of action currents by phenytoin in mammalian nerve", Epilepsia, Nov. 1994, 35(6), pp. 1279-1288.
Villavicencio, Alan T., "Laminectomy versus Percutaneous Electrode Placement for Spinal Cord Stimulation," Neurosurgery, vol. 46 (2), Feb. 2000, pp. 399-405.
Vleggeert, Lankamp et al., "Electrophysiology and morphometry of the Aalpha- and Abeta-fiber populations in the normal and regenerating rat sciatic nerve", Experimental Neurology, vol. 187, No. 2, Jun. 1, 2004, Available online Apr. 2, 2004, pp. 337-349.
Woessner, "Blocking Out the Pain, Electric Nerve Block Treatments for Sciatic Neuritis", Retrieved from http://www.practicalpainmanagement.com/pain/spine/radiculopathy/blocking-out-pain, Last updated Jan. 10, 2012.
Wolter et al., "Effects of sub-perception threshold spinal cord stimulation in neuropathic pain: A randomized controlled double-blind crossover study", European Federation of International Association for the Study of Pain Chapters, 2012, pp. 648-655.
Wu et al., "Changes in Aβ Non-nociceptive Primary Sensory Neurons in a Rat Model of Osteoarthritis Pain", Molecular Pain 6, No. 1 (Jul. 1, 2010): 37, doi:10.1186/1744-8069-6-37.

(56) References Cited

OTHER PUBLICATIONS

Xie et al., "Functional Changes in Dorsal Root Ganglion Cells after Chronic Nerve Constriction in the Rat", Journal of Neurophysiology 73, No. 5 (May 1, 1995): pp. 1811-1820.
Xie et al., "Sinusoidal Time-Frequency Wavelet Family and its Application in Electrograstrographic Signal Analysis", Proceedings of the 20th Annual International Conference of the IEEE Engineering in Medicine and Biology Society, vol. 20, No. 3, Oct. 29, 1998, pp. 1450-1453.
Yamada et al., "Extraction and Analysis of the Single Motor Unit F-Wave of the Median Nerve", EMG Methods for Evaluating Muscle and Nerve Function, InTech, 2012, 15 pgs.
Yearwood, T. L., "Pulse Width Programming in Spinal Cord Stimulation: a Clinical Study", Pain Physician. 2010. vol. 13, pp. 321-335.
Yingling et al., "Use of Antidromic Evoked Potentials in Placement of Dorsal Cord Disc Electrodes", Applied Neurophysiology, 1986, vol. 49, pp. 36-41.
Yuan, S. et al., "Recording monophasic action potentials using a platinum-electrode ablation catheter", Europace. Oct. 2000; 2(4): pp. 312-319.
Extended European Search Report for European Application No. 17778477.4, report completed Nov. 12, 2019, dated Nov. 20, 2019, 7 pgs.
Extended European Search Report for European Application No. 17814341.8, report completed Dec. 12, 2019, report dated Jan. 2, 2020, 8 pgs.
International Preliminary Report on Patentability for International Application No. PCT/AU2018/050278, dated Sep. 29, 2020, 7 pgs.
International Search Report and Written Opinion for International Application No. PCT/AU2018/050278, Search completed Jun. 18, 2018, dated Jun. 18, 2018, 12 Pgs.
International Search Report and Written Opinion for International Application No. PCT/AU2019/050384, Search completed Jun. 25, 2019, dated Jun. 25, 2019, 15 Pgs.
Japanese Office Action for Application No. 2017-546830, dated Feb. 20, 2020, 5 pages with English translation.
Japanese Office Action for Application No. 2017-553090, dated Mar. 16, 2020, 12 pages with English translation.
Japanese Office Action for Application No. 2018-513699, dated Jun. 8, 2020, 7 pages with English translation.
Office Action for Chinese Patent Application No. 201680020725.4, dated Mar. 16, 2020, 8 pgs.
Kopelman et al., "Attempted Reversible Sympathetic Ganglion Block by An Implantable Neurostimulator", Interactive Cardiovascular and Thoracic Surgery, Feb. 7, 2012, vol. 14, Issue 5, pp. 605-609.
International Preliminary Report on Patentability for International Application No. PCT/AU2019/050384, dated Oct. 27, 2020, 8 pgs.
Australian Examination Report for Application No. 2019283936, dated Apr. 1, 2021, 7 pages.
International Search Report and Written Opinion for International Application No. PCT/AU2019/051385, Search completed Mar. 24, 2020, dated Mar. 24, 2020, 8 Pgs.
International Search Report for International Application No. PCT/AU2019/051151, International Filing Date Oct. 22, 2019, Search Completed Feb. 24, 2020, dated Feb. 24, 2020, 9 pgs.
International Search Report for International Application No. PCT/AU2019/051160, International Filing Date Oct. 23, 2019, Search Completed Jan. 28, 2020, dated Jan. 28, 2020, 13 pgs.
International Search Report for International Application No. PCT/AU2019/051163, International Filing Date Oct. 23, 2019, Search Completed Jan. 21, 2020, dated Jan. 31, 2020, 8 pgs.
International Search Report for International Application No. PCT/AU2019/051197, International Filing Date Oct. 30, 2019, Search Completed Jan. 21, 2020, dated Jan. 21, 2020, 15 pgs.
International Search Report for International Application No. PCT/AU2019/051210, International Filing Date Nov. 2, 2019, Search Completed Feb. 4, 2020, dated Feb. 4, 2020, 10 pgs.
Japanese Office Action for Application No. 2018-552138, dated Mar. 1, 2021, 7 pages with English translation.

"Evoke 12C Percutaneous Leads", Saluda Medical, specifications available in the "Evoke Surgical Guide", version 6, http://www.saludamedical.com/manuals/, retrieved May 2017, 40 pgs.
Abrard et al., "A time-frequency blind signal separation method applicable to underdetermined mixtures of dependent sources", Signal Processing, vol. 85, 2005, pp. 1389-1403.
Baratta et al., "Orderly Stimulation of Skeletal Muscle Motor Units with Tripolar Nerve Cuff Electrode", IEEE Transactions on Biomedical Engineering, vol. 36, No. 8, Aug. 1989, pp. 836-842.
Casey et al., "Separation of Mixed Audio Sources by Independent Subspace Analysis", Mitsubishi Electric Research Laboratories, 2001, 8 pgs.
Celestin et al., "Pretreatment Psychosocial Variables as Predictors of Outcomes Following Lumbar Surgery and Spinal Cord Stimulation: A Systematic Review and Literature Synthesis", American Academy of Pain Medicine, 2009, vol. 10, No. 4, pp. 639-653. doi:10.1111/j.1526-4637.2009.00632.X.
Cong et al., "A 32-channel modular bi-directional neural interface system with embedded DSP for closed-loop operation", 40th European Solid State Circuits Conference (ESSCIRC), 2014, pp. 99-102.
Connolly et al., "Towards a platform for prototyping control systems for optimization of neuromodulation therapies", IEEE Biomedical Circuits and Systems Conference (BioCAS), 2015, pp. 1-4.
Delgado et al., "Measurement and interpretation of electrokinetic phenomena", Pure Appl. Chem., 2005, vol. 77, No. 10, pp. 1753-1805.
Fitzpatrick et al., "A Nerve Cuff Design for the Selective Activation and Blocking of Myelinated Nerve Fibers", IEEE Engineering in Medicine and Biology Society, vol. 13, No. 2, 1991, pp. 906-907.
Howell et al., "Evaluation of Intradural Stimulation Efficiency and Selectivity in a Computational Model of Spinal Cord Stimulation", Plos One, DOI:10.1371/journal.pone.0114938, Dec. 23, 2014, 25 pgs.
Jang et al., "Single Channel Signal Separation Using Time-Domain Basis Functions", IEEE Signal Processing Letters, Jun. 2003, vol. 10, No. 6, 13 pgs.
Jang et al., "A Maximum Likelihood Approach to Single-channel Source Separation", Journal of Machine Learning Research 4 (2003) 1365-1392.
Jones et al., "Scaling of Electrode-Electrolyte Interface Model Parameters In Phosphate Buffered Saline", IEEE Transactions on Biomedical Circuits and Systems, 2015, vol. 9, No. 3, pp. 441-448.
Kent, "Characterization of Evoked Potentials During Deep Brain Stimulation in the Thalamus", Dissertation, Duke University. Retrieved from https://hdl.handle.net/10161/8195, 2013, 320 pgs. https://dukespace.lib.duke.edu/dspace/handle/10161/8195.
Laird-Wah, "Improving Spinal Cord Stimulation: Model-Based Approaches to Evoked Response Telemetry", UNSW, Aug. 2015, 279 pgs.
Mannan et al., "Identification and Removal of Physiological Artifacts From Electroencephalogram Signals: A Review", IEEE Access, May 31, 2018 , vol. 6, p. 30630-30652, https://doi.org/10.1109/ACCESS.2018.2842082.
Niazy et al., "Removal of FMRI environment artifacts from EEG data using optimal basis sets", NeuroImage 28 (2005) 720-737.
North et al., "Prognostic value of psychological testing in patients undergoing spinal cord stimulation: a prospective study", Neurosurgery, Aug. 1, 1996, vol. 39, Issue 2, pp. 301-311. https://doi.org/10.1097/00006123-199608000-00013.
Peterson et al., "Stimulation artifact rejection in closed-loop, distributed neural interfaces", ESSCIRC, 42nd European Solid-State Circuits Conference, Lausanne, 2016, pp. 233-235.
Rijkhoff et al., "Acute Animal Studies on the Use of Anodal Block to Reduce Urethral Resistance in Sacral Root Stimulation", IEEE Transactions on Rehabilitation Engineering, vol. 2, No. 2, 1994, pp. 92-99.
Rijkhoff et al., "Orderly Recruitment of Motoneurons in an Acute Rabbit Model", Annual International Conference of the IEEE Engineering in Medicine and Biology Society, vol. 20, No. 5, 1998, pp. 2564-2565.
Scott et al., "Compact Nonlinear Model of an Implantable Electrode Array for Spinal Cord Stimulation (SCS)", IEEE Transactions on Biomedical Circuits and Systems, 2014, vol. 8, No. 3, pp. 382-390.

(56) References Cited

OTHER PUBLICATIONS

Stanslaski et al., "Design and Validation of a Fully Implantable, Chronic, Closed-Loop Neuromodulation Device With Concurrent Sensing and Stimulation", IEEE Transactions on Neural Systems and Rehabilitation Engineering, Jul. 2012, Date of Publication: Jan. 23, 2012, vol. 20, No. 4, pp. 410-421, DOI: 10.1109/TNSRE.2012.2183617.

Takahashi et al., "Classification of neuronal activities from tetrode recordings using independent component analysis", Neurocomputing, (2002), vol. 49, Issues 1-4, 289-298.

Zhang et al., "Automatic Artifact Removal from Electroencephalogram Data Based on A Priori Artifact Information", BioMed research international. 2015. 720450. Aug. 25, 2015, 9 pgs, DOI; https://doi.org/10.1155/2015/720450.

Zhou et al., "A High Input Impedance Low Noise Integrated Front-End Amplifier for Neural Monitoring", IEEE Transactions on Biomedical Circuits and Systems, 2016, vol. 10, No. 6, pp. 1079-1086.

\* cited by examiner

FEEDBACK CONTROL OF NEUROMODULATION

CROSS-REFERENCE TO RELATED APPLICATIONS

This application is a national stage of Application No. PCT/AU2017/050296, filed Apr. 5, 2017, which application claims the benefit of Australian Provisional Patent Application No. 2016901264, filed Apr. 5, 2016, the disclosures of which are incorporated herein by reference in their entireties.

TECHNICAL FIELD

The present invention relates to controlling a neural response to a stimulus, and in particular relates to measurement of a compound action potential by using one or more electrodes implanted proximal to the neural pathway, in order to provide feedback to control subsequently applied stimuli.

BACKGROUND OF THE INVENTION

There are a range of situations in which it is desirable to apply neural stimuli in order to give rise to an evoked compound action potential (ECAP). For example, neuromodulation is used to treat a variety of disorders including chronic neuropathic pain, Parkinson's disease, and migraine. A neuromodulation system applies an electrical pulse to neural tissue in order to generate a therapeutic effect.

When used to relieve neuropathic pain originating in the trunk and limbs, the electrical pulse is applied to the dorsal column (DC) of the spinal cord, referred to as spinal cord stimulation (SCS). Such a system typically comprises an implanted electrical pulse generator, and a power source such as a battery that may be rechargeable by transcutaneous inductive transfer. An electrode array is connected to the pulse generator, and is positioned adjacent the target neural pathway(s). An electrical pulse applied to the neural pathway by an electrode causes the depolarisation of neurons, and generation of propagating action potentials. The fibres being stimulated in this way inhibit the transmission of pain from that segment in the spinal cord to the brain. To sustain the pain relief effects, stimuli are applied substantially continuously, for example at a frequency in the range of 30 Hz-100 Hz.

For effective and comfortable operation, it is necessary to maintain stimuli amplitude or delivered charge above a recruitment threshold. Stimuli below the recruitment threshold will fail to recruit any action potentials. It is also necessary to apply stimuli which are below a comfort threshold, above which uncomfortable or painful percepts arise due to increasing recruitment of Aβ fibres which when recruitment is too large produce uncomfortable sensations and at high stimulation levels may even recruit sensory nerve fibres associated with acute pain, cold and pressure sensation. In almost all neuromodulation applications, a single class of fibre response is desired, but the stimulus waveforms employed can recruit action potentials on other classes of fibres which cause unwanted side effects. The task of maintaining appropriate neural recruitment is made more difficult by electrode migration and/or postural changes of the implant recipient, either of which can significantly alter the neural recruitment arising from a given stimulus, depending on whether the stimulus is applied before or after the change in electrode position or user posture. There is room in the epidural space for the electrode array to move, and such array movement alters the electrode-to-fibre distance and thus the recruitment efficacy of a given stimulus. Moreover the spinal cord itself can move within the cerebrospinal fluid (CSF) with respect to the dura. During postural changes the amount of CSF and the distance between the spinal cord and the electrode can change significantly. This effect is so large that postural changes alone can cause a previously comfortable and effective stimulus regime to become either ineffectual or painful.

Another control problem, facing neuromodulation systems of all types, is achieving neural recruitment at a sufficient level required for therapeutic effect, but at minimal expenditure of energy. The power consumption of the stimulation paradigm has a direct effect on battery requirements which in turn affects the device's physical size and lifetime. For rechargeable systems, increased power consumption results in more frequent charging and, given that batteries only permit a limited number of charging cycles, ultimately this reduces the implanted lifetime of the device.

Attempts have been made to address such problems by way of feedback, such as by way of the methods set forth in International Patent Publication No. WO2012155188 by the present applicant. Feedback seeks to compensate for nerve and/or electrode movement by controlling the delivered stimuli so as to maintain a constant ECAP amplitude.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood that the element may be any one of the listed options, or may be any combination of two or more of the listed options.

SUMMARY OF THE INVENTION

According to a first aspect the present invention provides an automated method of controlling a neural stimulus, the method comprising:

applying the neural stimulus to a neural pathway in order to give rise to an evoked action potential on the neural pathway, the stimulus being defined by at least one stimulus parameter;

measuring a neural compound action potential response evoked by the stimulus, and deriving from the measured evoked response a feedback variable;

completing a feedback loop by using the feedback variable to control the at least one stimulus parameter value; and adaptively compensating for changes in a gain of the feedback loop caused by electrode movement relative to the neural pathway, by applying a compensating transfer function to the feedback variable, the compensating transfer function being configured to compensate for both (i) a distance-dependent transfer function of stimulation, and (ii) a distance dependent transfer function of measurement which is distinct from (i).

According to a second aspect the present invention provides an implantable device for controllably applying a neural stimulus, the device comprising:

a plurality of electrodes including one or more nominal stimulus electrodes and one or more nominal sense electrodes;

a stimulus source for providing a stimulus to be delivered from the one or more stimulus electrodes to a neural pathway in order to give rise to an evoked action potential on the neural pathway;

measurement circuitry for recording a neural compound action potential signal sensed at the one or more sense electrodes; and a control unit configured to:

control application of a neural stimulus as defined by at least one stimulus parameter;

measure via the measurement circuitry a neural compound action potential response evoked by the stimulus;

determine from the measured evoked response a feedback variable; complete a feedback loop by using the feedback variable to control the at least one stimulus parameter value; and adaptively compensate for changes in a gain of the feedback loop caused by electrode movement relative to the neural pathway, by applying a compensating transfer function to the feedback variable, the compensating transfer function being configured to compensate for both (i) a distance-dependent transfer function of stimulation and (ii) a distance dependent transfer function of measurement which is distinct from (i).

According to a third aspect the present invention provides a non-transitory computer readable medium for controllably applying a neural stimulus, comprising the following instructions for execution by one or more processors:

computer program code means for applying the neural stimulus to a neural pathway in order to give rise to an evoked action potential on the neural pathway, the stimulus being applied as defined by at least one stimulus parameter;

computer program code means for measuring a neural compound action potential response evoked by the stimulus and deriving from the measured evoked response a feedback variable;

computer program code means for completing a feedback loop by using the feedback variable to control the at least one stimulus parameter value; and computer program code means for adaptively compensating for changes in a gain of the feedback loop caused by electrode movement relative to the neural pathway, by applying a compensating transfer function to the feedback variable, the compensating transfer function being configured to compensate for both (i) a distance-dependent transfer function of stimulation and (ii) a distance dependent transfer function of measurement which is distinct from (i).

The present invention recognises that (i) recruitment of evoked compound action potentials upon the neural pathway by a given stimulus will vary based on the distance of the stimulus electrode(s) from the neural pathway, and (ii) the observed waveform of a given ECAP from the neural pathway will vary based on the distance of the sense electrode(s) from the neural pathway, and moreover that the transfer function for (i) differs from the transfer function for (ii), so that electrode movement as may be caused by patient movement, postural changes, heartbeat or the like will affect the recruitment behaviour of a system using feedback control of the stimulus.

Some embodiments may provide a control method for effecting constant recruitment by use of single I & V measurements (where I is a measure of stimulus current, and V is a measure of observed ECAP voltage), rather than having to estimate or measure a stimulus threshold or response growth curve. In such embodiments that transfer function preferably comprises a single parameter k reflecting both a recruitment parameter n and a measurement parameter m, m and n being unequal because the stimulation transfer function differs from the measurement transfer function. For example, where the total number of fibres recruited N varies with distance x as $\propto Ix^{-n}-T_0$, and the measured ECAP voltage amplitude V is approximated as $V \propto Nx^{-m}$, then in some embodiments $k=m/n$. Importantly, the present invention recognises that the feedback parameter k is not equal to 1, because the stimulation transfer function differs from the measurement transfer function. The feedback parameter k is preferably selected to take a value which is suitable for the stimulation and recording configurations in use, such as a value which depends on a distance from a stimulation electrode(s) to recording electrode(s), and/or which depends on a stimulation electrode to reference electrode configuration, and/or which depends on a stimulation configuration whether bipolar stimulation or tripolar stimulation or the like. For example in one such configuration in which tripolar stimulation is delivered using the first to third electrodes of a SCS lead, and recordings are taken using the sixth electrode of the same lead, the feedback parameter k is preferably selected to be in the range 0-0.8, more preferably 0.1 to 0.7, more preferably 0.16 to 0.61, more preferably 0.22 to 0.53, more preferably 0.3 to 0.43, most preferably about 0.37.

In some embodiments of the invention k is determined clinically using a recruitment datum. The recruitment datum may comprise one or more of the patient's perceptual threshold, discomfort threshold, coverage of a certain area or body part, a qualitative characteristic of the patient's perception of a stimulation such as optimal comfort, an electrophysiological measure, such as the onset of muscle response/twitching, or a measure of neural activity. Such measures may use the amplitude, latency or other characteristic(s) of responses evoked by the stimulus, which may appear in the spine, the peripheral nerves, the brain, or elsewhere in the body. In such embodiments clinical determination of k may comprise the patient assuming a series of postures; in each posture adjusting the stimulus intensity until the required recruitment datum is achieved; and estimating k from constant recruitment data in differing postures by a suitable fitting or approximation.

In some embodiments of the invention k is determined clinically by using the recording electrode to measure neural responses to peripheral stimulation, such as constant TENS stimulation, in a number of postures to obtain Vi data in each posture. The peripheral stimulation may then be removed and the stimulus electrodes of the implant may then deliver stimulation in each posture adjusted to a current level Ii which yields the respective Vi and is thus known to have achieved constant recruitment independently of posture. The set of $(I_i, V_i)$ pairs of constant recruitment may then be fitted or approximated to yield k.

In some embodiments of the invention, particularly for applications involving fibre populations having a narrow range of fibre diameters, k may be determined clinically by placing the patient in a range of postures i, and in each posture sweeping the stimulus intensity and recording a growth curve. From the growth curve for each respective posture, a line is fitted to a linear portion of the curve to determine the threshold $T_i$ and growth slope $M_i$. Plotting the values of log $T_i$ against log $T_iM_i$; and fitting a line to these points gives a slope $-m/n=-k$.

In some embodiments, n and m are treated as constants which approximate the power law applicable to the respective transfer function throughout the operating domain. However, alternative embodiments may provide for variable n and/or variable m, for example to reflect that n and m may reduce slightly, and by differing degrees, with higher recruitment. Such adaptivity in n and m may be implemented so as to provide more accurate compensation depending on whether the device is operating in a regime of low or high recruitment.

Some embodiments of the invention may thus implement a feedback loop as follows: Incoming measurements of ECAPs (V) are multiplied with an exponentiated version ($I^{-k}$) of the stimulus current (I) used to generate them. An error signal is generated relative to a setpoint and fed into a controller G, which determines the next stimulus intensity. I-V control can thus be implemented as a feedback loop, controlling a term of the form $F=I^kV$ with error signal $e=\hat{F}-F$ derived from the chosen setpoint $\hat{F}$.

The feedback variable could in some embodiments be any one of: an amplitude; an energy; a power; an integral; a signal strength; or a derivative, of any one of: the whole evoked compound action potential; the fast neural response for example in the measurement window 0-2 ms after stimulus; the slow neural response for example in the measurement window 2-6 ms after stimulus; or of a filtered version of the response. The feedback variable could in some embodiments be an average of any such variable determined over multiple stimulus/measurement cycles. The feedback variable may in some embodiments be the zero intercept, or the slope, of a linear portion of the response of ECAP amplitude to varying stimulus current. In some embodiments the feedback variable may be derived from more than one of the preceding measures.

The control variable, or stimulus parameter, could in some embodiments be one or more of the total stimulus charge, stimulus current, pulse amplitude, phase duration, interphase gap duration or pulse shape, or a combination of these.

The present invention thus recognises that using a feedback loop to maintain a constant ECAP is a difficult task as changes in patient posture both create signal inputs and change the loop characteristics of both (i) the stimulation electrode to nerve transfer function, and (ii) the nerve to sense electrode transfer function.

The set point of the feedback loop may be configured so as to seek a constant value of ECAP amplitude, or may be configured to seek a target ECAP amplitude which changes over time, for example as defined by a therapy map as described in International Patent Application Publication No. WO2012155188 by the present applicant, the content of which is incorporated herein by reference.

BRIEF DESCRIPTION OF THE DRAWINGS

An example of the invention will now be described with reference to the accompanying drawings, in which.

DESCRIPTION OF THE PREFERRED EMBODIMENTS

Figure 1:
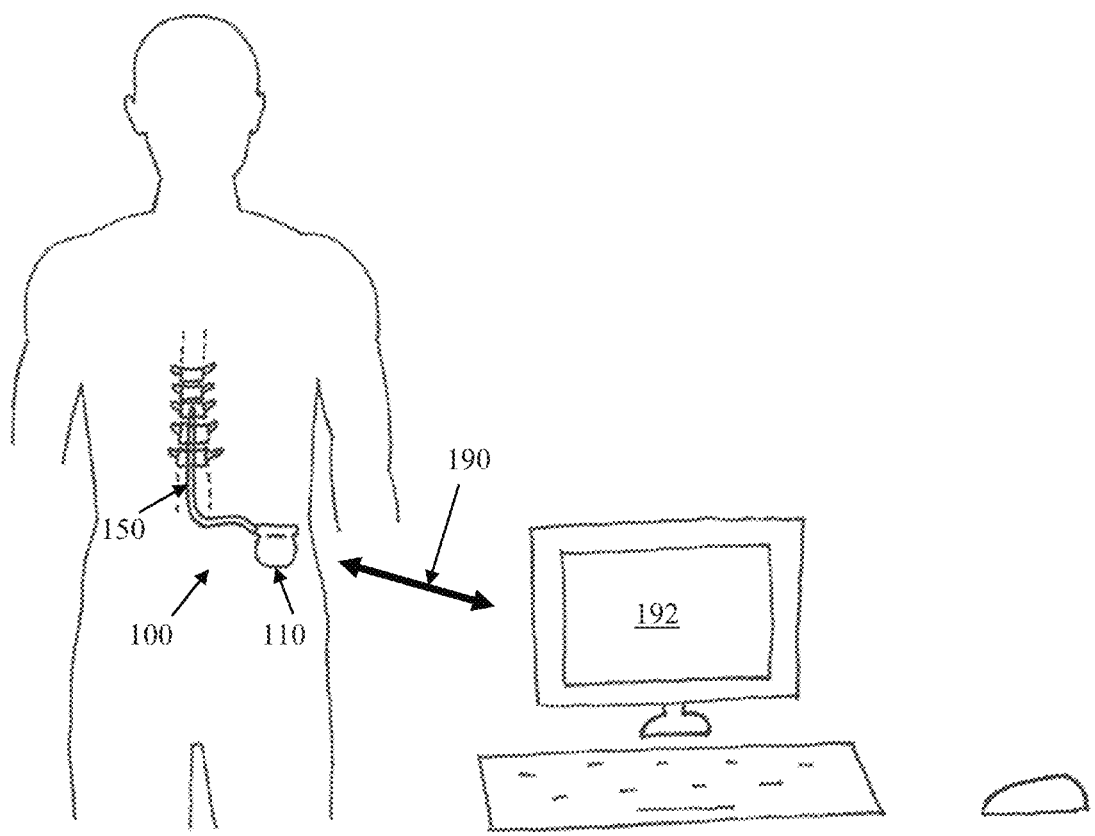
FIG. 1 schematically illustrates an implanted spinal cord stimulator.

FIG. 1 schematically illustrates an implanted spinal cord stimulator 100. Stimulator 100 comprises an electronics module 110 implanted at a suitable location in the patient's lower abdominal area or posterior superior gluteal region, and an electrode assembly 150 implanted within the epidural space and connected to the module 110 by a suitable lead. Numerous aspects of operation of implanted neural device 100 are reconfigurable by an external control device 192. Moreover, implanted neural device 100 serves a data gathering role, with gathered data being communicated to external device 192.

Figure 2:
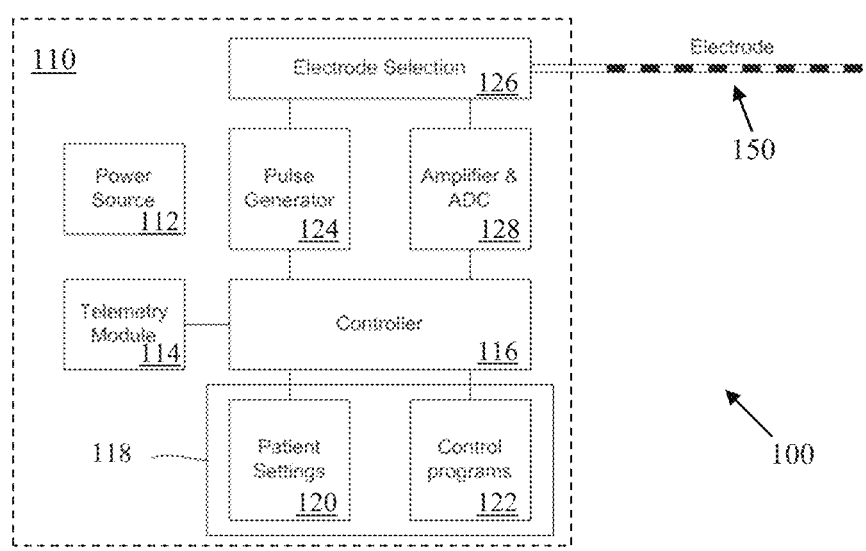
FIG. 2 is a block diagram of the implanted neurostimulator.

FIG. 2 is a block diagram of the implanted neurostimulator 100. Module 110 contains a battery 112 and a telemetry module 114. In embodiments of the present invention, any suitable type of transcutaneous communication 190, such as infrared (IR), electromagnetic, capacitive and inductive transfer, may be used by telemetry module 114 to transfer power and/or data between an external device 192 and the electronics module 110.

Module controller 116 has an associated memory 118 storing patient settings 120, control programs 122 and the like. Controller 116 controls a pulse generator 124 to generate stimuli in the form of current pulses in accordance with the patient settings 120 and control programs 122. Electrode selection module 126 switches the generated pulses to the appropriate electrode(s) of electrode array 150, for delivery of the current pulse to the tissue surrounding the selected electrode(s). Measurement circuitry 128 is configured to capture measurements of neural responses sensed at sense electrode(s) of the electrode array as selected by electrode selection module 126.

Figure 3:
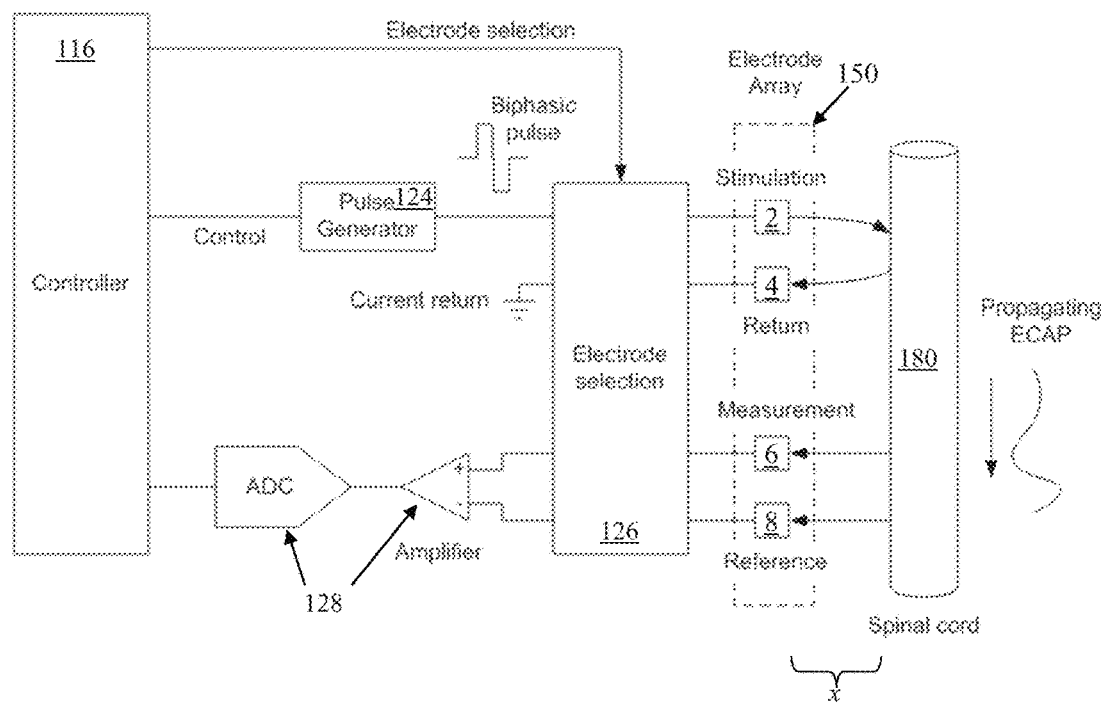
FIG. 3 is a schematic illustrating interaction of the implanted stimulator with a nerve.

FIG. 3 is a schematic illustrating interaction of the implanted stimulator 100 with a nerve 180, in this case the spinal cord however alternative embodiments may be positioned adjacent any desired neural tissue including a peripheral nerve, visceral nerve, parasympathetic nerve or a brain structure. Electrode selection module 126 selects a stimulation electrode 2 of electrode array 150 to deliver an electrical current pulse to surrounding tissue including nerve 180, and also selects a return electrode 4 of the array 150 for stimulus current recovery to maintain a zero net charge transfer.

Delivery of an appropriate stimulus to the nerve 180 evokes a neural response comprising a compound action potential which will propagate along the nerve 180 as illustrated, for therapeutic purposes which in the case of a spinal cord stimulator for chronic pain might be to create paraesthesia at a desired location. To this end the stimulus electrodes are used to deliver stimuli at 30 Hz. To fit the device, a clinician applies stimuli which produce a sensation that is experienced by the user as a paraesthesia. When the paraesthesia is in a location and of a size which is congruent with the area of the user's body affected by pain, the clinician nominates that configuration for ongoing use.

The device 100 is further configured to sense the existence and intensity of compound action potentials (CAPs) propagating along nerve 180, whether such CAPs are evoked by the stimulus from electrodes 2 and 4, or otherwise evoked. To this end, any electrodes of the array 150 may be selected by the electrode selection module 126 to serve as measurement electrode 6 and measurement reference electrode 8. Signals sensed by the measurement electrodes 6 and 8 are passed to measurement circuitry 128, which for example may operate in accordance with the teachings of International Patent Application Publication No. WO2012155183 by the present applicant, the content of which is incorporated herein by reference.

The present invention recognises that in attempting to implement a feedback control loop, there are two distance-dependent transfer functions involved in ECAP recording. The first is in stimulation: at a greater distance x, a higher current is needed to stimulate the same nerve fibres. The second is in recording: at a greater distance x, a given neural recruitment results in a smaller observed ECAP. Feedback seeking a constant observed ECAP voltage amplitude takes no account of the recording transfer function, with the result that recruitment will actually increase as the cord distance increases. Moreover, the first and second transfer functions are unequal and require separate compensation.

The present invention provides an approach which considers both distance-dependent transfer functions, in a manner which is responsive to the differences between the transfer functions, to thereby improve the performance of feedback control.

Such a method is necessarily limited by the impossibility or at least impracticality of directly measuring neural recruitment in humans via intracellular patch clamp recording or the like; it must be possible in a practical feedback system to fit feedback parameters to the patient without such measurements.

Figure 4:
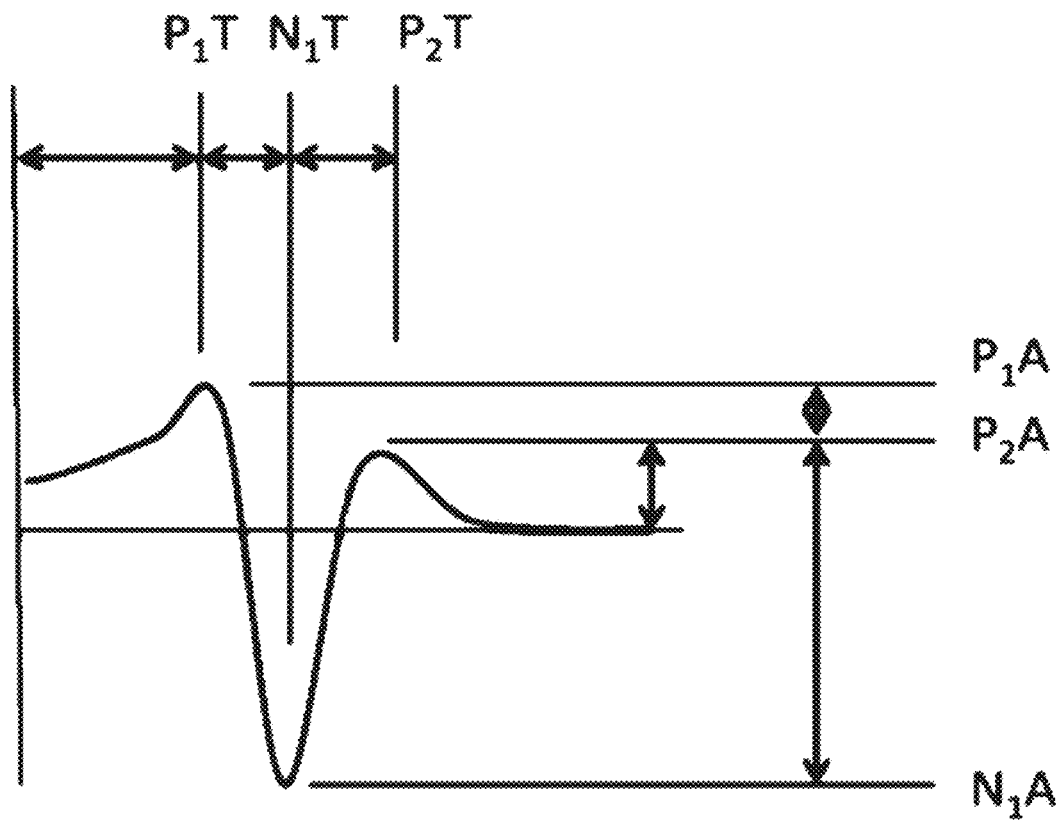
FIG. 4 illustrates the typical form of an electrically evoked compound action potential.

FIG. 4 illustrates the typical form of an electrically evoked compound action potential of a healthy subject. The shape of the compound action potential shown in FIG. 4 is predictable because it is a result of the ion currents produced by the ensemble of axons generating action potentials in response to stimulation. The action potentials generated among a large number of fibres sum to form a compound action potential (CAP). The CAP is the sum of responses from a large number of single fibre action potentials. The CAP recorded is the result of a large number of different fibres depolarising. The propagation velocity is determined largely by the fibre diameter. The CAP generated from the firing of a group of similar fibres is measured as a positive peak potential $P_1$, then a negative peak $N_1$, followed by a second positive peak $P_2$. This is caused by the region of activation passing the recording electrode as the action potentials propagate along the individual fibres. An observed CAP signal will typically have a maximum amplitude in the range of microvolts.

The CAP profile takes a typical form and can be characterised by any suitable parameter(s) of which some are indicated in FIG. 4. Depending on the polarity of recording, a normal recorded profile may take an inverse form to that shown in FIG. 4, i.e. having two negative peaks $N_1$ and $N_2$, and one positive peak $P_1$.

Figure 5:
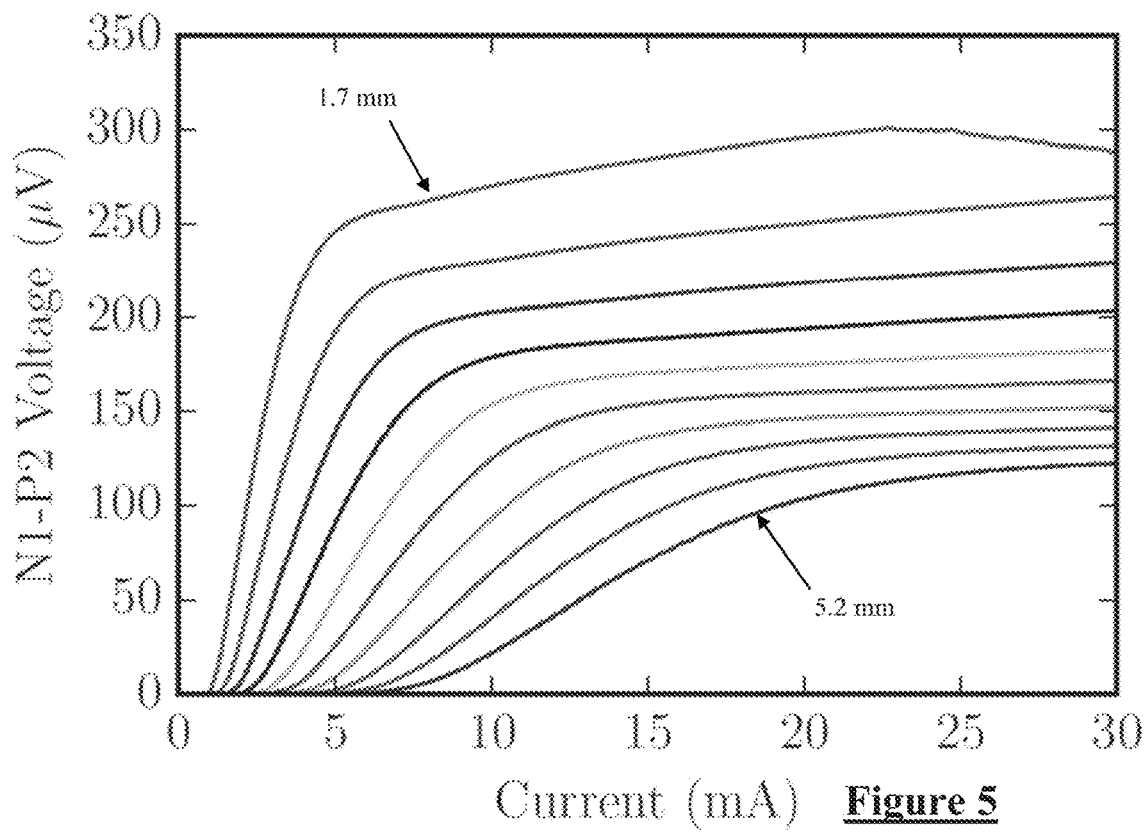
FIG. 5 is a plot of the peak-to-peak amplitude of observed ECAPs.

For purposes of illustration, ECAP simulations were performed with an SCS model for each of 10 different cord positions, varying the cord-electrode distance from 1.7 mm to 5.2 mm (1.7 mm, 2.1 mm, 2.5 mm, 2.9 mm, 3.3 mm, 3.6 mm, 4.0 mm, 4.4 mm, 4.8 mm, 5.2 mm). Monophasic stimuli were used to avoid confounding measurements with the second-cathode effect. An 8-electrode linear array is modelled, as is commonly used in SCS. Stimuli are delivered on electrode 2 with current returned on electrodes 1 and 3. FIG. 5 is a plot of the peak-to-peak amplitude of the ECAPs observed on electrode 6 at these cord-electrode distances in response to stimulus currents in the range of 0-30 mA. As can be seen, as the cord is moved closer to the electrode array, the recruitment threshold is lowered and the growth slope and saturation amplitude increase.

Figure 6:
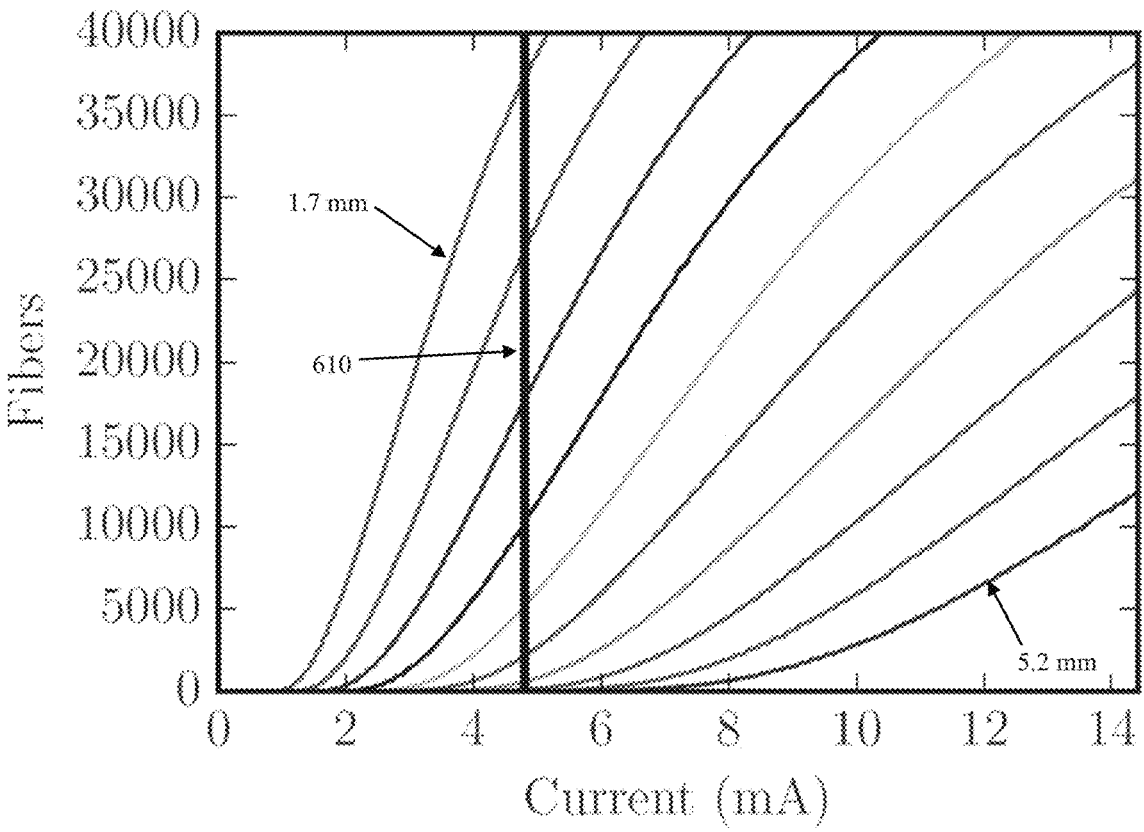
FIG. 6 is a plot of recruitment as a function of current.

In order to compare stimulation methods, a target recruitment of 5000 fibres is chosen; this is within the linear recruitment region, as commonly observed in therapeutic stimulation. FIG. 6 is a plot of recruitment as a function of current, illustrating the use of a fixed stimulus amplitude (vertical line 610) in accordance with prior art approaches. The fixed current amplitude (approx. 4.8 mA) is chosen to recruit 5000 fibres at the medial cord position. The number of fibres recruited using a constant stimulus current ranges from zero fibres to nearly 35000 fibres across the examined cord positions. This highlights the degree to which traditional SCS is sensitive to cord position.

Figure 7:
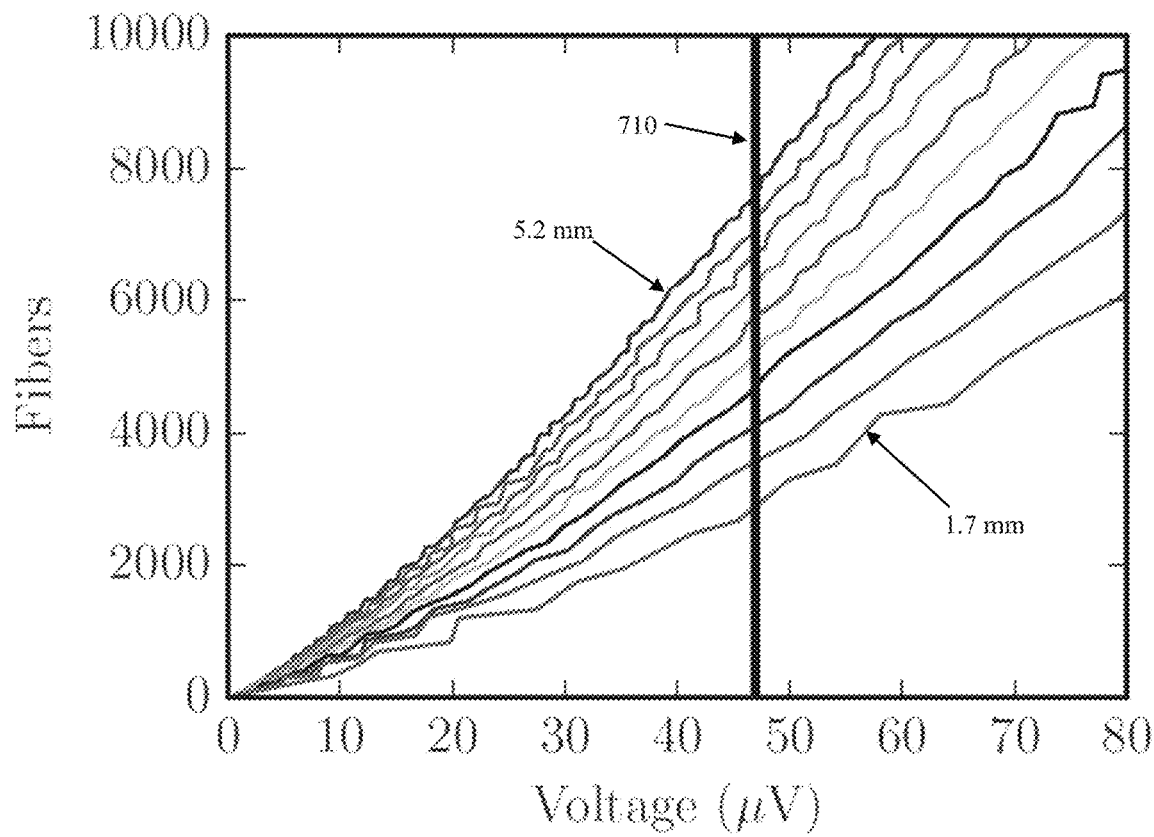
FIG. 7 illustrates recruitment as a function of recording amplitude.

FIG. 7 illustrates recruitment as a function of recording amplitude, when using feedback control which seeks a constant N1-P2 recording amplitude (vertical line 710). The set amplitude (approx. 47 µV) is chosen so as to recruit 5000 fibres at the medial cord position. Compared to the constant stimulus amplitude approach of FIG. 6, the recruitment variation resulting from electrode-nerve separation changes in FIG. 7 is reduced, with recruitment now varying from approximately 3000 to 6500 fibres across the distances examined. It is noted that the variation in FIG. 7 is reversed as compared to the constant-current stimulation approach of FIG. 6: in FIG. 7 the recruitment is increased at larger cord distances. Nevertheless, the constant observed voltage approach of FIG. 7 continues to suffer from a considerable degree of undesired recruitment variation in response to changes in electrode-to-nerve separation, with recruitment being almost 40% less than desired when electrode-to-nerve separation is 1.7 mm, and being almost 60% greater than desired when electrode-to-nerve separation is 5.2 mm.

The present invention thus recognises that when the electrode-to-nerve separation is subject to change, the constant stimulus approach of FIG. 6 and the constant observed voltage approach of FIG. 7 both fail to reliably recruit the desired therapeutic number of neural fibres.

The present invention instead provides for feedback control of stimulus amplitude in a manner which compensates for both (i) the stimulus transfer function relative to electrode-to-nerve separation x and (ii) the recording transfer function relative to electrode-to-nerve separation x, and does so in a manner which accounts for the differences between (i) and (ii).

Both the stimulus transfer function and the recording transfer function describe a physical process where a first element (stimulation electrode or nerve, respectively) radiates an electric field in a volume conductor, and some of this field is sensed by a second element (nerve or sense electrode, respectively). The coupling of a radiative process typically falls off with some power of the distance, and can be modelled by equations including such a power term. Importantly, however, the stimulation transfer function is not the same as (nor the inverse of) the measurement transfer function, at least due to the differing originating waveforms (pulsatile stimulus vs. a typically 3-lobed ECAP waveform), due to the differing electrode configurations invariably employed to deliver stimulation on the one hand and to obtain neural measurements on the other hand, and due to the increasing dispersion of the ECAP waveform as it travels away from the stimulation site, at least.

In order to address the unequal transfer functions appropriately, we first derive an expression for the relationship between the stimulus intensity I and the number of recruited fibres N, i.e. the stimulation transfer function. This function will depend on the distance x between the target tissue and the stimulating electrodes. N will be equal to the number of fibres with thresholds lower than the stimulus intensity; these thresholds $T_i$ will also vary with distance:

$$N = \sum_i [I > T_i(x)]$$

The change in $T_i$ with x can be approximated by a simple analytic model. If we consider a single myelinated nerve fibre exposed to a point current source at distance x and with internodal length L, the voltage at the qth node of Ranvier is of the form:

$$\frac{I}{\sqrt{x^2 + (qL)^2}}$$

where $q \in \mathbb{Z}$ and assuming that the $0^{th}$ node is at the point on the fibre nearest the electrode.

The propensity of the fibre to be activated by a given stimulus is approximated by a function known as the activating function. This represents the net depolarisation current being applied to each node of Ranvier on the fibre, and has a threshold behaviour; if the depolarisation is sufficient at any node, the fibre will fire. For a myelinated fibre, the activating function is given by the second difference of the field along the fibre. This has a maximum at the node nearest the electrode, with value $$I\left(\frac{2}{\sqrt{x^2}} - \frac{1}{\sqrt{x^2+L^2}} - \frac{1}{\sqrt{x^2-L^2}}\right)$$

Thus the threshold will vary with distance as $$T_i \propto \left(\frac{1}{x} - \frac{1}{\sqrt{x^2+L^2}}\right)^{-1}$$

This is not a particularly tractable expression. The internodal spacing in the dorsal columns is generally less than the cord-electrode distance; in the region L≪x, the fourth and higher derivatives of $T_i$ are quite small, and the behaviour approximates $$T_i \propto x^n$$

For the case of the monopolar point source stimulation, $n \in [1,3]$. In other configurations of electrodes, surrounding tissue, and nerves, the value of n may be outside this range.

Applying this to the ensemble behaviour, the total number of fibres recruited by a given stimulus depends on the fibre thresholds $T_i$. In the linear region of recruitment growth, N increases linearly with I, so the $T_i$ can be assumed uniformly distributed, and the number recruited varies as $$N \propto Ix^{-n} - T_0$$

where $T_0$ is a normalised threshold corresponding to the threshold of the most sensitive fibres at x=1.

From this derivation, it can be seen that the power n (also referred to as the stimulation transfer function parameter) will depend on the electrical and geometric relationship between stimulation electrodes and stimulated tissue. For example, with the use of multipolar stimulus electrode configurations as commonly found in therapeutic SCS, the near-field activating function may be increased due to the increased variation in the field, while the far-field may fall off more quickly due to dipole cancellation. These effects also depend on the geometry of the stimulated nerve fibres, and on the electrical properties of the intervening and surrounding tissues; for example, the longitudinal anisotropic conductivity of the white matter of the dorsal columns affects the field shape. The stimulus intensity I in the presently described embodiments is stimulus current, although alternative stimulus intensity parameters (voltage, pulse width, etc) may equivalently be used.

Figure 8:
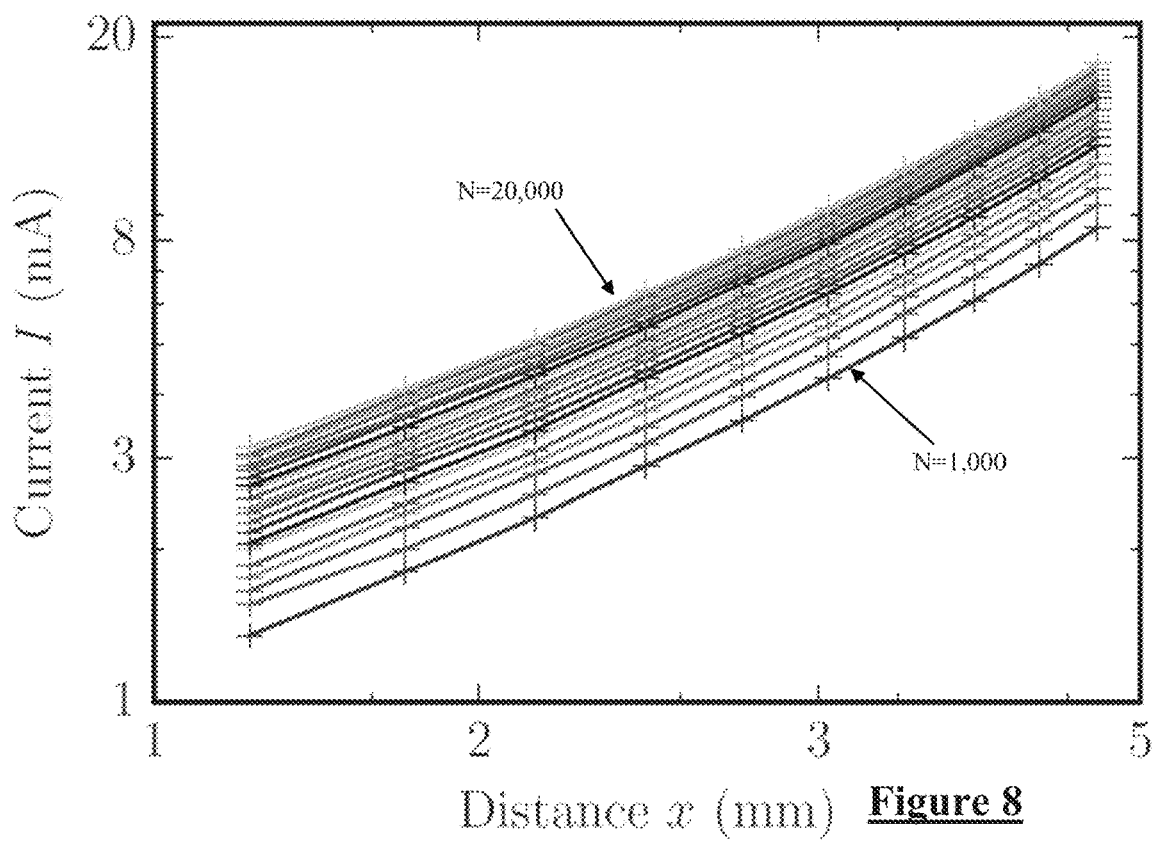
FIG. 8 illustrates the corresponding stimulus current for each distance x.

This relationship is examined using the ECAP model results. For a given recruitment value N, the corresponding stimulus current for each distance x is calculated. This is shown in FIG. 8 for recruitment values up to N=20,000, within the linear portion of the recruitment curve. The lines in FIG. 8 are not exactly straight, indicating that recruiting the same number of fibres at larger distances requires disproportionately higher current, indicating a shift in the power law. Treating n as a constant allows the slopes of the curves to be used as an estimate for n: using linear regression over log-log axes results in n≈1.64 at low recruitment (N=1,000), dropping to n≈1.55 at higher recruitment levels (N=20,000).

As noted in the preceding, it is necessary to not only address the stimulation transfer function, it is also necessary to address the recording transfer function. Thus, we derive an expression for the recording transfer function; being the relationship between the number of recruited fibres N and the observed $N_1$-$P_2$ ECAP amplitude V, although other measures of ECAP intensity may equivalently be used. The recorded signal V varies in a distance-dependent manner with the neural recruitment. The action potential results from a region of depolarisation which effectively propagates between nodes of Ranvier; this also results in membrane currents both ahead of and behind the depolarisation, effectively producing a field commensurate with a double dipole or tripole source. The propagation of an action potential along a myelinated fibre is too complex for meaningful analytical treatment; instead, simulation can be undertaken of a collection of myelinated nerve fibres with a point recording electrode, for which it has been found that the single fibre action potential (SFAP) amplitude $S_i$ of a single fibre at distance x followed a law $$S_i \propto x^{-m}$$

where m=1 close to the fibre, and m=3 in the far field. The former is expected where x<<L, and the nearest node's action current dominates the recording; the latter results from the approximately tripolar nature of the travelling action potential.

The ECAP voltage V results from the summation of many single fibre action potentials (SFAPs), and thus depends on the spatial and diametric distribution of recruited fibres. Different diameter fibres have different SFAP amplitudes, however the present embodiment of the invention notes that their proportions are fairly constant over the linear portion of the growth curve. The present embodiment of the invention further assumes that the spatial distribution of recruited fibres varies less than x, which enables us to approximate the ECAP amplitude as:

$$V \propto Nx^{-m} \qquad (2)$$

where m is a recording transfer function parameter.

In practice, the recording electrodes are not points, but physical structures of significant dimensions compared to the nerves and/or nerve-electrode distance. Differential recording is often used, where the ECAP is measured as a difference in potential between two electrodes in proximity to the target tissue. The ECAP also undergoes changes in waveform as it propagates away from the point of initiation due to dispersion, fibre termination and so forth. The surrounding electrical environment also affects the recording transfer. The membrane properties of the nerve fibres also affect the depolarisation behaviour and hence the induced external currents. These and other factors introduce additional influences on m.

From these derivations, it can be seen that n depends on factors including the stimulus electrode configuration, including configuration of drive and return electrodes; dimension and placement of electrodes; conductive properties of surrounding tissues; and the nerve fibre geometries. Meanwhile, m depends on factors including the recording electrode (and reference electrode, if used); the membrane properties and geometries of the individual nerve fibres; the overall neural population stimulated; and the surrounding tissues. Thus it is expected that m and n will take different values, and may further vary with the current cord-electrode distance.

Figure 9:
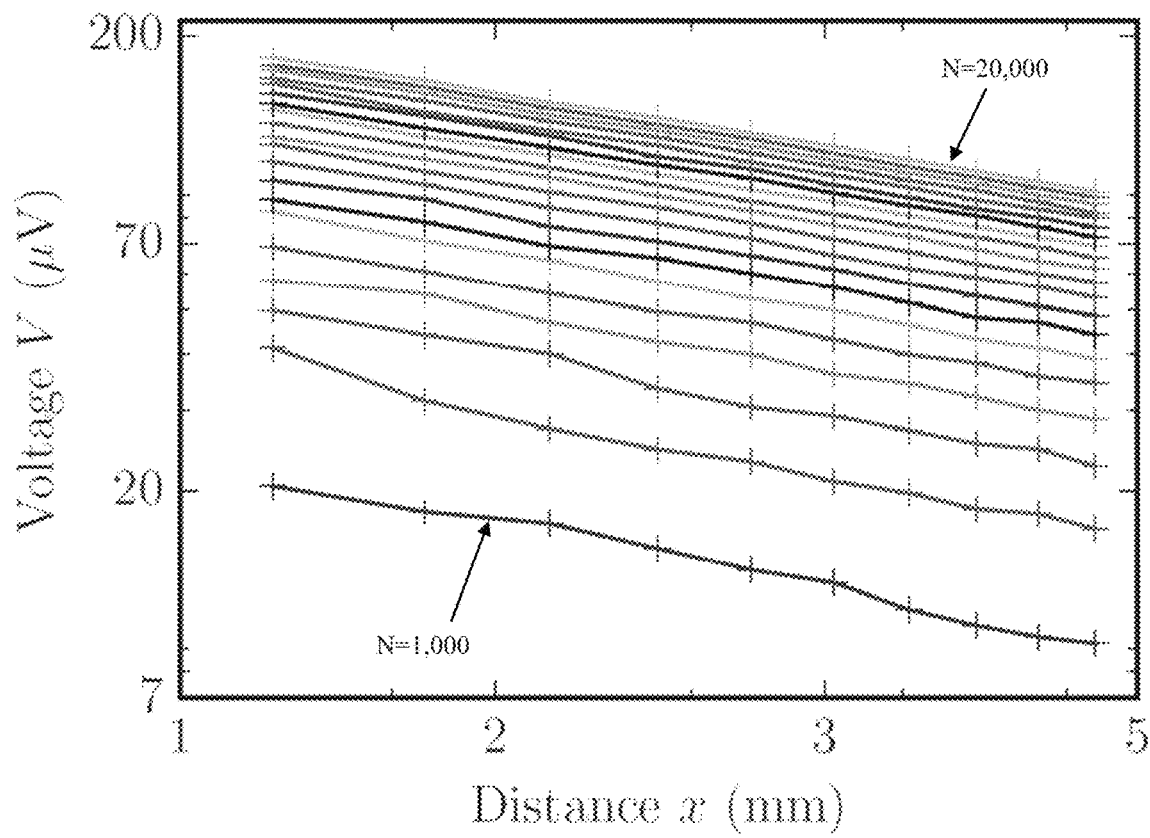
FIG. 9 shows voltage-distance curves calculated from the ECAP model.

The recording transfer function in the ECAP model is examined using voltage distance curves at constant recruitments. FIG. 9 shows voltage-distance curves calculated from the ECAP model results. Each line shows the relationship between ECAP amplitude and distance, for a fixed recruitment ranging from N=1000 (bottom curve) to N=20,000 (top curve) in steps of 1000, on log-log axes. The slope of each line is an estimate of the value −m. These curves indicate values form of about 0.75 at the beginning of recruitment (small N), with m dropping to about 0.6-0.65 over the linear region. Without intending to be limited by theory, it may be that the decreasing value of m corresponds to the broadening of the range of recruited fibre diameters, whereby the diameter-dependent conduction velocity of myelinated fibres results in a dispersion of the action potential volley; this results in a longer region of the nerve trunk that is contributing to the ECAP via membrane currents. The triphasic field radiated by each fibre then cancels somewhat, resulting in a field that falls off more rapidly with distance.

The stimulation transfer function parameter n and the recording transfer function parameter m can be determined as they are related to the electrode geometry and configuration and are not expected to change appreciably during therapy. The distance x is not known, however the stimulation transfer function and the recording transfer function can be combined to compensate for the changes in x and ensure constant recruitment. The stimulation current I can be known, and the ECAP voltage V can be measured, on each stimulus. Substituting equation (2) into equation (1) gives:

$$N \propto I\left(\frac{AN}{V}\right)^{-n/m} - T_0 \qquad (3)$$

where A is the constant of proportionality of equation 2.

In order to maintain constant N, as is desired for feedback control, it follows that $I^{m/n}V$ must be constant. For the purpose of recruitment control, this is most easily expressed as:

$$y = I^k V \qquad (4)$$

where k=m/n and k>0.

This embodiment of the invention thus captures the transfer function behaviour in a single parameter k which, being derived from m and n, reflects both the stimulation transfer function and the recording transfer function and, importantly, reflects that these transfer functions are not the same, as discussed in the preceding, and is configured to compensate for both unique transfer functions.

Figure 17:
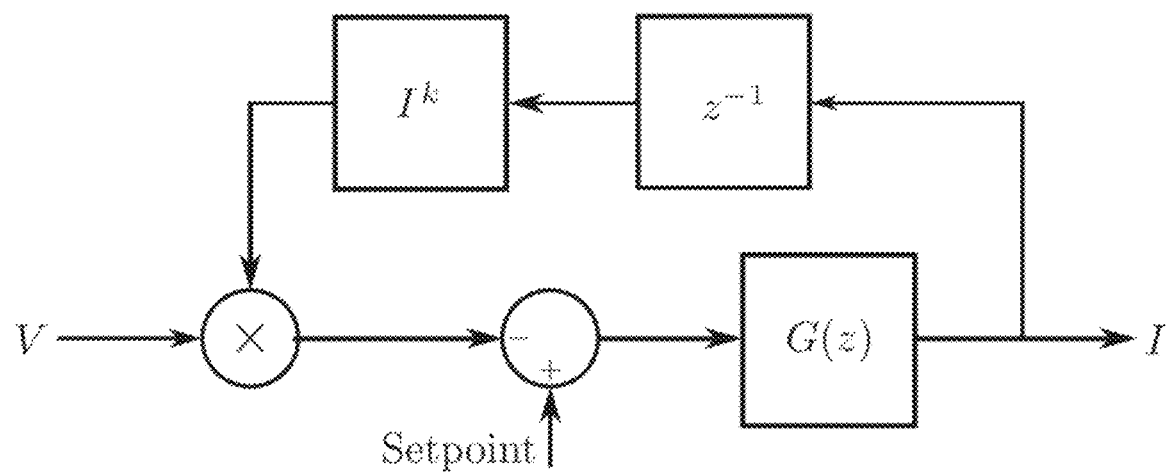
FIG. 17 illustrates a feedback loop to maintain constant recruitment, using I-V control.

The stimulus current I can then be adjusted using any suitable feedback algorithm (such as is shown in FIG. 17, discussed further below) to maintain the relationship between I and V, with the desired value of y being driven to a chosen set-point. A higher value of y will result in higher recruitment.

Figure 10:
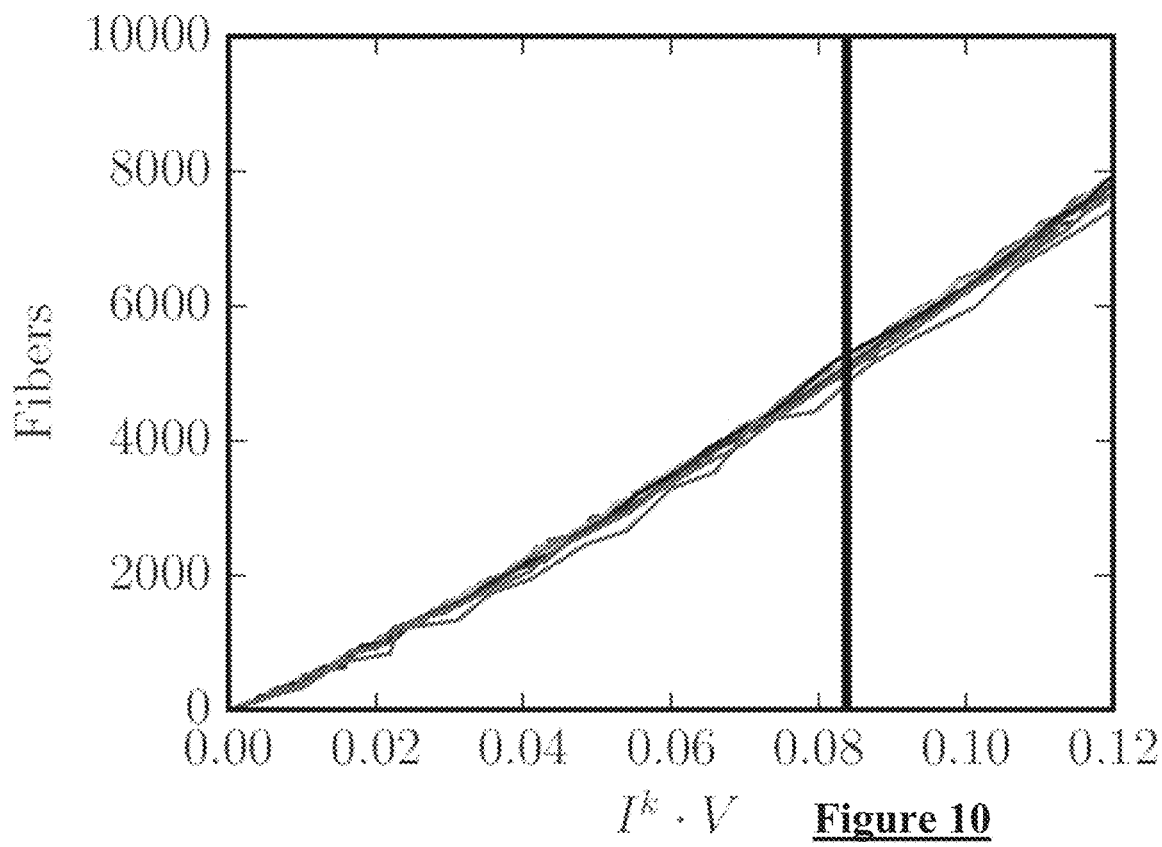
FIG. 10 illustrates the relationship between $I^kV$ value and recruitment.

The performance of this feedback method is examined by measuring the setpoint-recruitment curve for various distances. For this comparison, m and n were estimated to be 0.6 and 1.6, respectively, giving a value of k=0.37. The relationship between $I^k V$ value and recruitment is shown in FIG. 10.

Figure 11A:
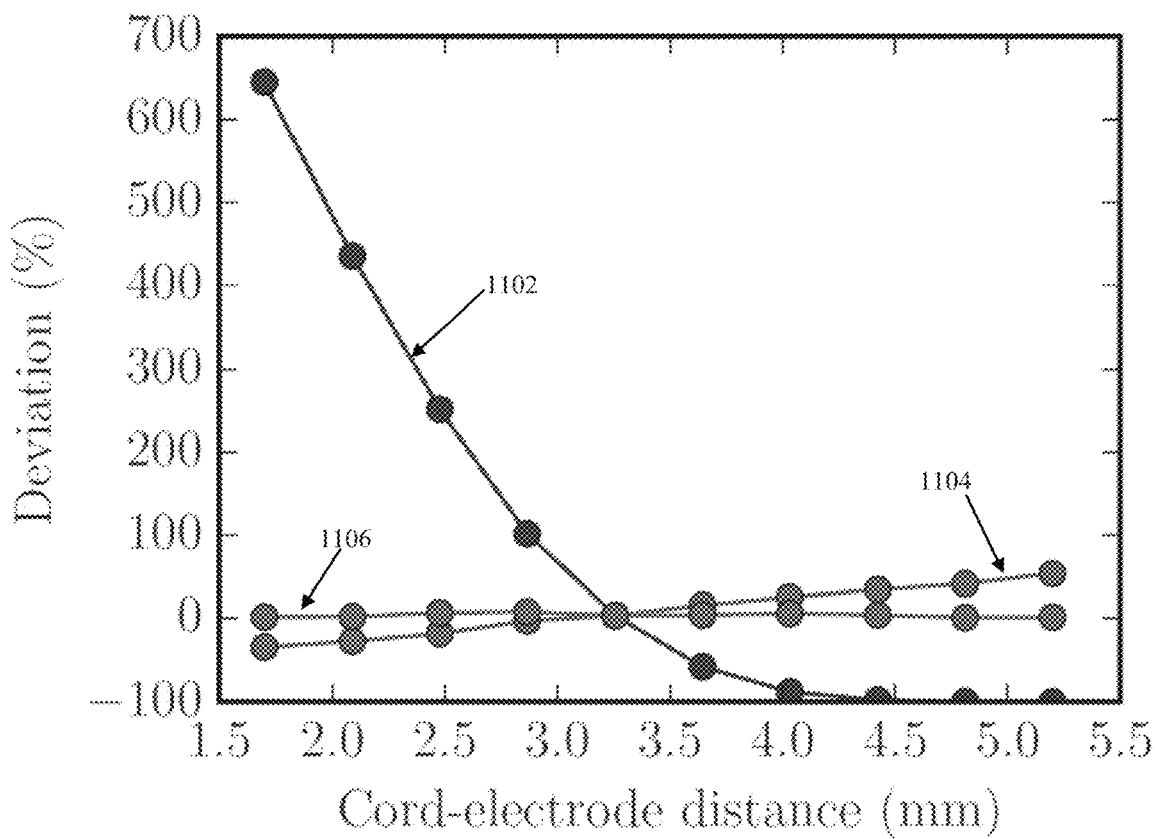
FIGS. 11a and 11b illustrate performance of the previous constant current approach, the previous constant ECAP voltage approach, and the I-V approach.
Figure 11B:
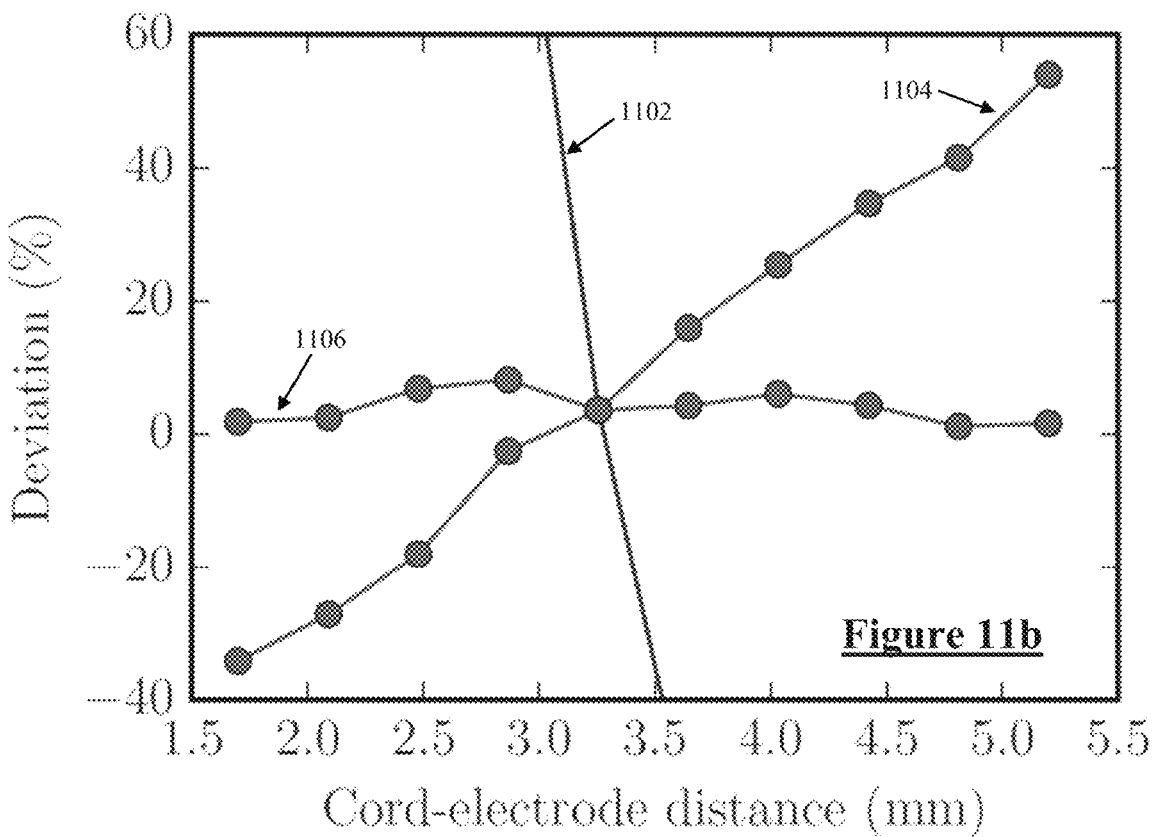

The setpoint shown in the figure is chosen for N=5,000 fibre recruitment at a cord-electrode distance x of 3.2 mm, in the middle of the range. Across the full range of cord positions, ranging from 1.7 mm to 5.2 mm, the recruitment remains within a narrow range demonstrating the benefit of this embodiment of the invention, and illustrating that an assumption of n and m being constant performs well. FIG. 11a illustrates performance of the previous constant current approach 1102, the previous constant ECAP voltage 1104, as compared to the present embodiment 1106. The extremely poor performance of constant-current stimulation 1102 is visible in the full view of FIG. 11a; the detail view of FIG. 11b shows the improved performance of the present embodiment's I-V control 1106 over constant-amplitude control 1104. Constant-amplitude control 1104 results in variations of greater than −30/+50% from the setpoint, while I-V control 1106 maintains constant recruitment to better than ±5%.

Figure 12:
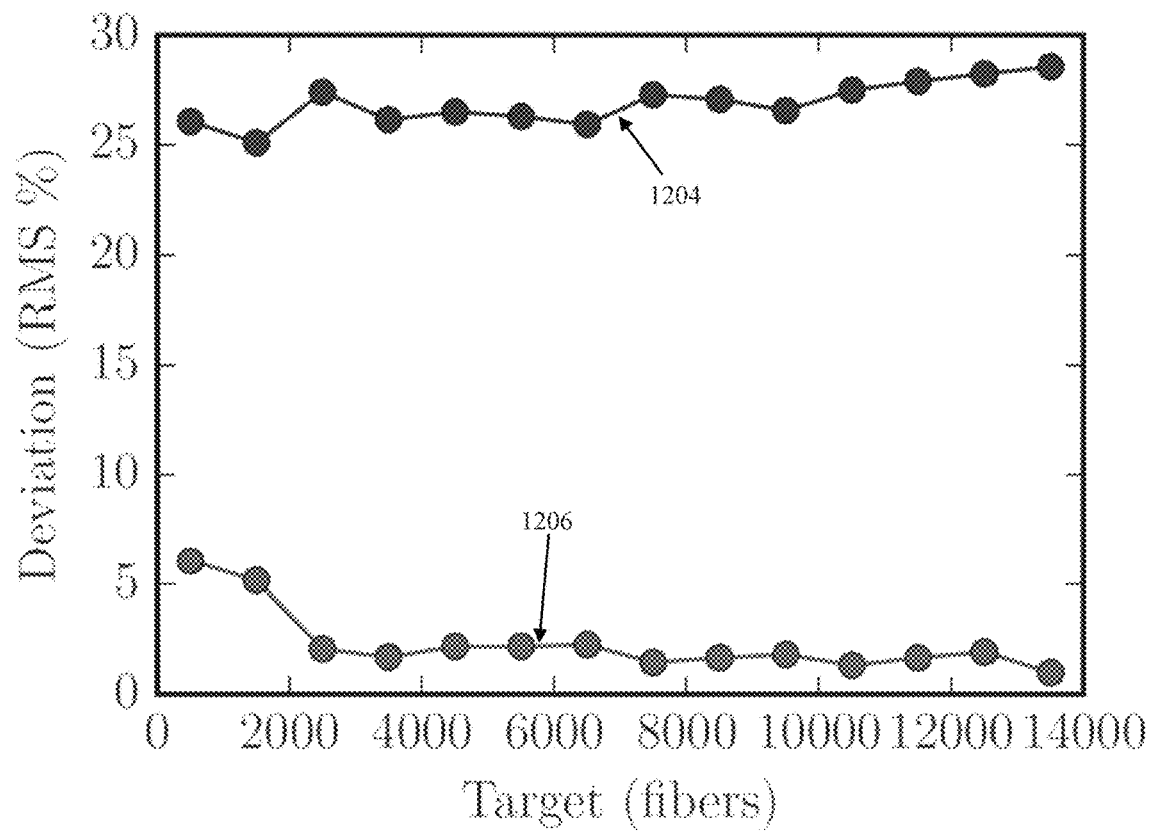
FIG. 12 illustrates performance of the I-V approach across a range of desired recruitment values.

Moreover, the I-V control 1206 performs consistently well across a range of desired recruitment values, as shown in FIG. 12. For each desired recruitment, a suitable setpoint was determined for each algorithm, again using the cord distance of 3.2 mm. The recruitment was calculated for each cord position with that setpoint, and the RMS deviation from the mean recorded. I-V control 1206 results in less variation in recruitment (typically <5%) across a wide range of setpoints as compared to the previous constant ECAP approach 1204 (typically >25%).

Figure 13:
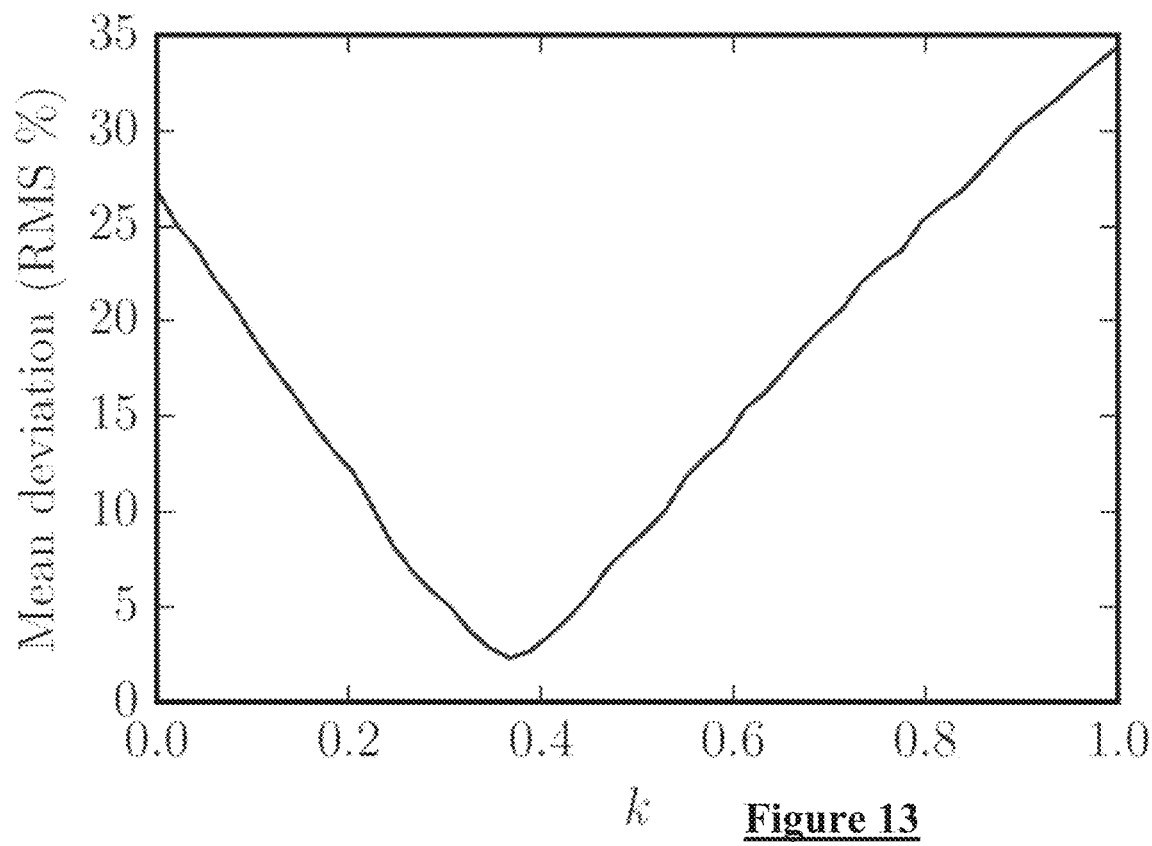
FIG. 13 illustrates the overall error for each value of k.

The I-V control method of the present embodiment requires that a suitable value for k to be chosen. A sensitivity analysis was conducted, varying k between 0 and 1. For each value, an RMS deviation measurement was made of the type shown in FIG. 12. The overall error for each value of k was estimated by averaging the RMS deviation for all considered recruitment levels, shown in FIG. 13. With k=0, the current term (I) is removed from the feedback equation, making I-V control equivalent to constant-amplitude control with relatively poor mean deviation (RMS) of over 25%. FIG. 13 shows that I-V control outperforms constant-amplitude control for any value of k between 0 and 0.8.

In such a simulation, suitable ranges of k to achieve given performance can be read directly off FIG. 13, for example to achieve mean deviation less than 20% k should be set 0.1 to 0.7, less than 15% mean deviation gives k 0.16 to 0.61, less than 10% mean deviation gives k 0.22 to 0.53, less than 5% mean deviation gives k 0.3 to 0.43, least mean deviation gives k about 0.37. However, in practice the plot of FIG. 13 is not available and indirect measures are required in order to determine k in order to fit an implant to a recipient, as discussed further below.

Figure 14:
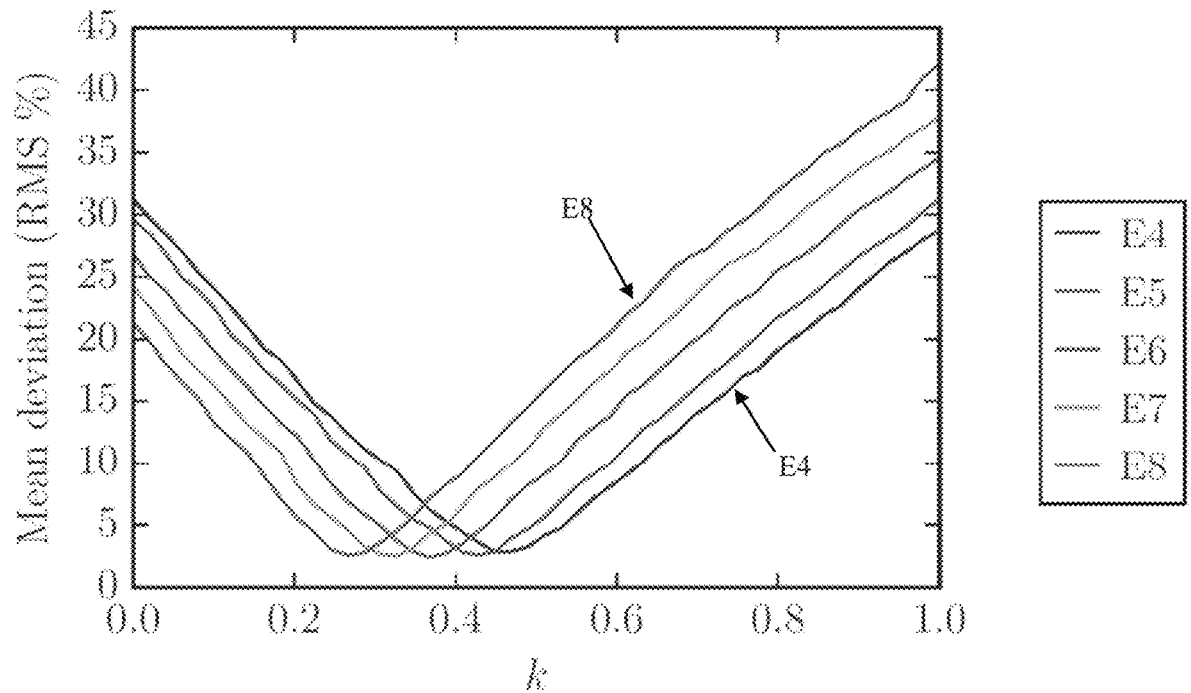
FIG. 14 illustrates variation in k between electrodes.

The recording transfer function of equation (2) depends on the recording electrode in use. Geometric factors may differ between electrodes, and the dispersion of the action potential volley increases as it travels away from the stimulation site. Increasing dispersion decreases m, so the correct value of k can be expected to be lower with increasing distance from the stimulus. This is seen in FIG. 14. If recording on electrode 4, closest to the stimulus, the optimal k is approximately 0.45, but any value between 0 and 1 outperforms constant-amplitude feedback. For electrode 8, the optimal value is approximately 0.27, with values between 0 and 0.55 outperforming constant-amplitude.

Figure 15:
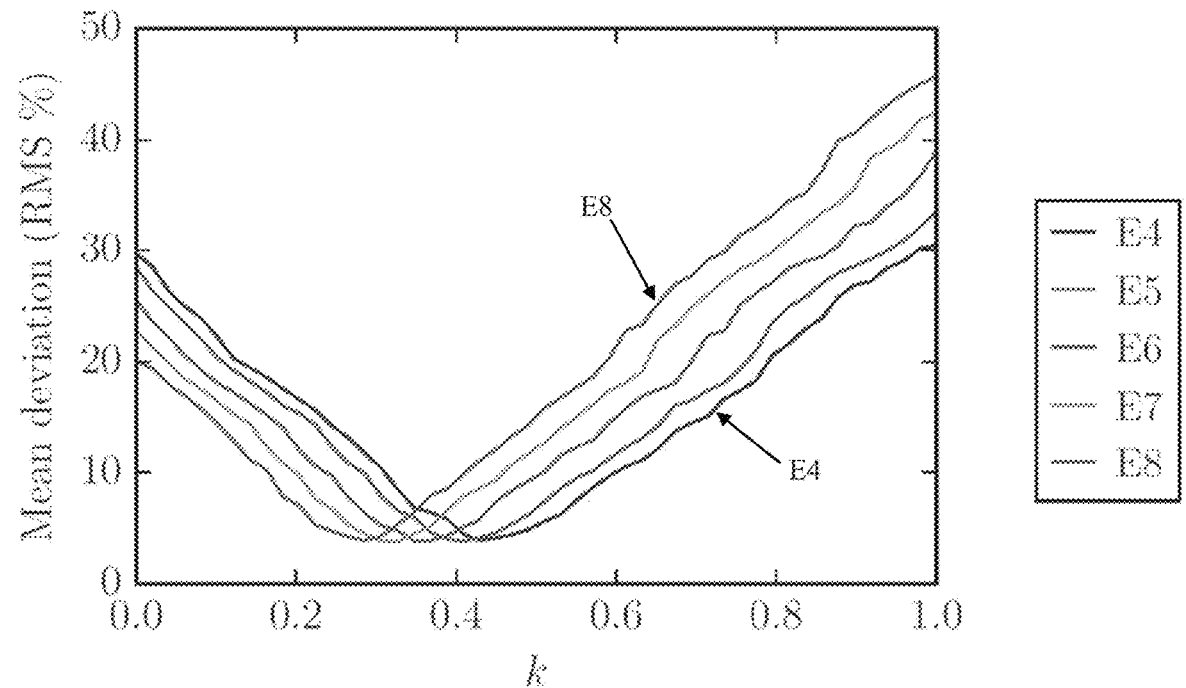
FIG. 15 shows the effect of different values of k on the performance of the I-V technique, with biphasic stimulation and on different electrodes.
Figure 16:
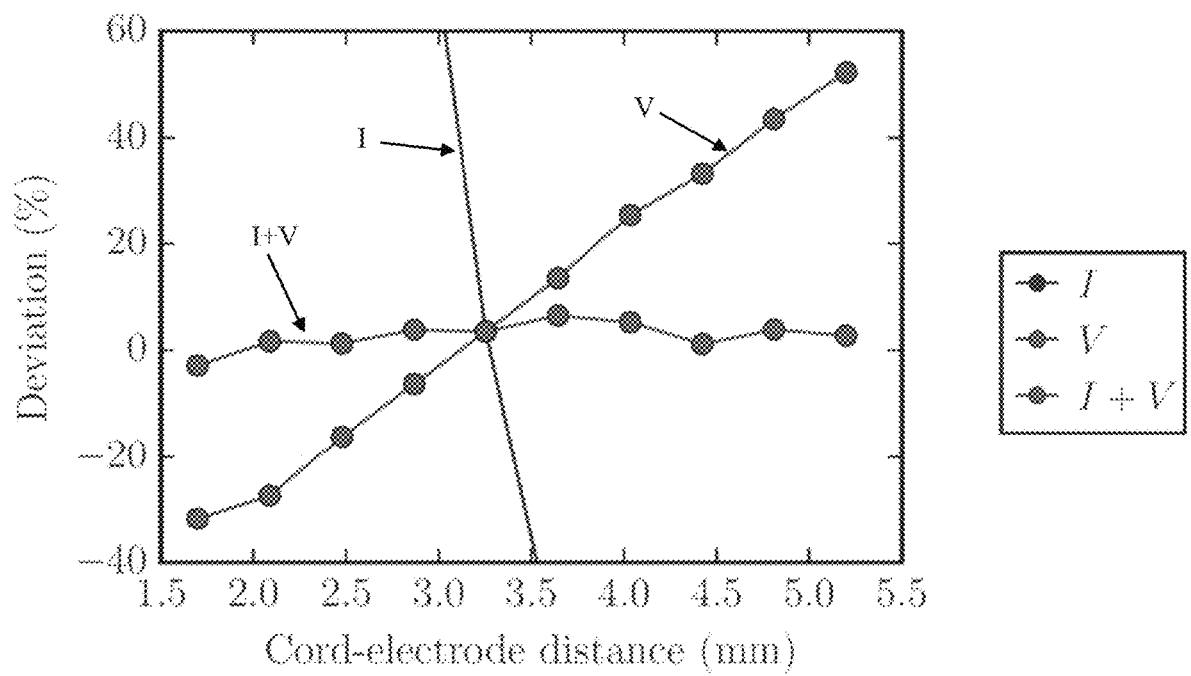
FIG. 16 shows the performance of I, V, and I-V control with biphasic stimulation.

The results of FIGS. 5 to 14 were prepared using monophasic stimulation, in order to clearly demonstrate the principles without consideration of the second cathode effect and its complication of results. However, the techniques described are equally applicable when biphasic stimulation is used, as shown in FIGS. 15 and 16. In particular, FIG. 15 shows the effect of different values of k on the performance of the present technique of recruitment control, with biphasic stimulation and on different electrodes. The best results obtained in the biphasic stimulus case are similar to those in the monophasic case, although the optimal value for k is somewhat lower. I-V control in the biphasic case outperforms constant-amplitude control for k values between 0 and 0.65. FIG. 16 shows the performance of I, V, and I-V control with biphasic stimulation. A k-value of 0.35 was used for I-V control. Voltage mode (V) control results in a variation of greater than −30/+50% across the examined range of distances, while I-V control maintains recruitment within less than +10/−0% of the initial setpoint.

The I-V control method thus requires a single parameter, k, which will depend on the patient's spinal geometry as well as the stimulation and recording configuration. In some embodiments of the invention, k can be determined from a precomputed table or almanac, where a fixed value is chosen based on one or more of the stimulation and recording parameters. For example, the distance between stimulation and recording electrode, the stimulus pulse-width, and the location of the measurement reference electrode may be used to determine the optimal value of k.

In some embodiments of the invention k can be determined clinically, using a recruitment datum. A recruitment datum can be used as a reference point to adjust the stimulus intensity and achieve the same level of neural recruitment in different postures. Suitable data may include the patient's perceptual threshold, discomfort threshold, coverage of a certain area or body part, or any qualitative characteristic of the patient's perception of a stimulation such as optimal comfort. Electrophysiological measures may also be used, such as the onset of muscle response/twitching, or some measure of neural activity. Such measures may use the amplitude, latency or other characteristic(s) of responses evoked by the stimulus, which may appear in the spine, the peripheral nerves, the brain, or elsewhere in the body.

In this embodiment, the patient is instructed to assume a series of postures, achieving a different but unknown cord-electrode distance $x_i$ in each. In each posture, the stimulus intensity is adjusted until the recruitment datum is achieved. The resulting current $I_i$ and ECAP measure $V_i$ are recorded for each posture i. Since the use of the recruitment datum implies that N is constant across these measurements, this implies that $$I_i \propto x_i^n$$

$$V_i \propto x_i^{-m}$$

Thus, one simple method to estimate $I_i$ is to plot log $I_i$ against log $V_i$ and fit a line to these data points; this line would then have a slope of −n/m=−k. Other methods for approximating solutions to such equations may also be used.

Other methods which recruit a constant subpopulation of nerve fibres may also be used for this task. For example, peripheral nerve stimulation using transdermal electrical nerve stimulation (TENS) can provide constant recruitment of a peripheral nerve, even as the patient's posture changes; if some subset of these peripheral nerves extend into the spine in the vicinity of the recording electrode, then an evoked signal $V_i$ can be recorded in each posture i. After recording $V_i$ in each posture, the peripheral stimulus is removed, and the therapeutic stimulus introduced; its intensity is adjusted to reproduce an evoked response of amplitude equal to $V_i$, and this intensity $I_i$ recorded. This procedure produces a set of $(I_i, V_i)$ pairs of constant recruitment, which may be fitted for k as with other recruitment datum data.

Alternative embodiments may however seek to determine k directly from ECAP recordings, without reference to the patient's percept. The recording transfer function between recruitment, distance, and ECAP amplitude is complex, particularly as it depends on the dispersion characteristics of the recruited fibre population. Amplitude measurements alone cannot always distinguish changes in dispersion from changes in recruitment. However, a fitting technique is presented here which is suitable for fibre populations which have a very narrow range of diameters. Although this is not the case in the spinal column the following technique may be useful elsewhere in the body when using a single recording electrode. In some cases, particularly where the fibre population is fairly homogeneous, it is possible to determine k from threshold and slope measurements of the growth curve.

In a typical growth curve, there is a linear region where the measured variable grows linearly with the stimulus intensity. Therapeutic SCS operates in the linear region. The growth curves shown in FIG. 5 show such a linear region; for example at a cord-electrode distance of 1.7 mm, this region extends between 1.5 mA and 3 mA; at 5.2 mm, this extends approximately between 9 mA and 18 mA. Such a linear region can be characterised by fitting a line to it; it is then described by the slope M and the x-intercept (threshold)

T of that line. The ECAP measurement V in this linear region can then be modelled as a function of stimulus intensity I:

$$V = M(I-T)$$

It is then apparent, when considering the power law models of stimulation and recording transfer functions, that $$T \propto x^n$$

$$M \propto x^{-(m+n)}$$

Thus, a method for estimating k is to place the patient in a range of postures i, and in each posture, sweep the stimulus intensity and record a growth curve. From each growth curve, a line is fitted determining the threshold $T_i$ and growth slope $M_i$. The values of log $T_i$ can be plotted against log $T_i M_i$; a line fitted to these points then has slope $-m/n = -k$. Other methods for finding solutions to these equations may alternatively be used.

FIG. 17 illustrates a feedback loop to maintain constant recruitment, using I-V control in accordance with the present embodiment. Incoming measurements of ECAPs (V) are multiplied with an exponentiated version ($I^k$) of the stimulus current (I) used to generate them. An error signal is generated relative to the setpoint and fed into a controller G, which determines the next stimulus intensity. I-V control can thus be implemented as a feedback loop in the manner shown. The setpoint is a unitless value determined by the patient's desired level of stimulation. A discrete-time controller G(z) is used to control the stimulus current based on the error signal; this may take the form of a simple gain or a more complex system such as a PID controller.

This particular scheme has the potential to improve loop response speed in addition to providing better control accuracy. In constant-amplitude feedback, the patient's transfer function (from stimulus to ECAP amplitude) varies with posture; this limits the maximum controller gain that can be applied while keeping the loop stable, and in doing so limits the potential bandwidth. If I-V control is implemented by scaling the ECAP amplitude at the input to G(z), then when the loop is tracking correctly the scaling compensates for the changing transfer function of the patient. This means that the gain of G(z) can be maximised without compromising stability, increasing the speed with which the loop can respond.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not limiting or restrictive.

The invention claimed is:

1. An automated method of controlling a neural stimulus, the method comprising:
    applying the neural stimulus to a neural pathway in order to give rise to an evoked action potential on the neural pathway, the stimulus being defined by at least one stimulus parameter;
    measuring a neural compound action potential response evoked by the stimulus, and deriving from the measured evoked response (ECAP) a feedback variable;
    completing a feedback loop by using the feedback variable to control the at least one stimulus parameter value; and
    adaptively compensating for changes in a gain of the feedback loop caused by electrode movement relative to the neural pathway, by applying a compensating transfer function to the feedback variable, the compensating transfer function including the at least one stimulus parameter as a variable and being configured to compensate for both (i) a distance-dependent transfer function of stimulation, and (ii) a distance dependent transfer function of measurement which is distinct from the distance-dependent transfer function of stimulation; wherein applying the compensating transfer function comprises multiplying the feedback variable with an exponentiated version ($I^k$) of the stimulus parameter (I) used to generate that ECAP.

2. The method of claim 1 wherein constant recruitment is effected by use of single measurement pairs of stimulus parameter (I) and observed ECAP amplitude (V).

3. The method of claim 1 wherein the parameter k reflects both a recruitment parameter n and a measurement parameter m, m≠n.

4. The method of claim 3 wherein the total number of fibres recruited N varies as $N \propto I x^{-n} - T_0$, where x is the electrode to cord distance, the measured ECAP amplitude V is approximated as $\propto N x^{-m}$, and $k = m/n$.

5. The method of claim 4 wherein k is selected to take a value which is based upon the stimulation and recording configurations in use.

6. The method of claim 5 wherein tripolar stimulation is delivered using first to third electrodes of a SCS lead, and recordings are taken using a sixth electrode of the same lead, and wherein k is selected to be in the range 0.1 to 0.7.

7. The method of claim 6 wherein k is selected to be in the range 0.22 to 0.53.

8. The method of claim 7 wherein k is selected to be about 0.37.

9. The method of claim 3 wherein k is determined clinically using a recruitment datum.

10. The method of claim 9 wherein the recruitment datum comprises one or more of: the patient's perceptual threshold, discomfort threshold, coverage of a certain area or body part, a qualitative characteristic of the patient's perception of a stimulation, patient's perception of optimal comfort, an electrophysiological measure, the onset of muscle response/twitching, and a measure of neural activity.

11. The method of claim 9 further comprising the patient assuming a series of postures; in each posture adjusting the stimulus parameter until the required recruitment datum is achieved; and estimating k from constant recruitment data in differing postures.

12. The method of claim 3 wherein k is partly or wholly determined clinically by using the recording electrode to measure neural responses to peripheral stimulation in a number of postures to obtain Vi data in each posture; using the stimulus electrode to deliver stimulation in each posture adjusted to a current level Ii which yields the respective Vi, and using the set of ($I_i$, $V_i$) pairs of constant recruitment to derive k.

13. The method of claim 3 wherein k is partly or wholly determined clinically by placing the patient in a range of postures i, in each posture sweeping the stimulus parameter and recording a growth curve, linearly fitting the growth curve for each respective posture to determine the respective threshold $T_i$ and growth slope $M_i$, and comparing log $T_i$ against log $T_i M_i$; to derive k.

14. The method of claim 1 wherein an error signal is generated from the compensated feedback variable relative to a setpoint and fed into a controller which determines the next stimulus parameter value.

15. The implantable device of claim 1, wherein the feedback variable is an amplitude of the measured evoked response.

16. An implantable device for controllably applying a neural stimulus, the device comprising:
- a plurality of electrodes including one or more nominal stimulus electrodes and one or more nominal sense electrodes;
- a stimulus source for providing a stimulus to be delivered from the one or more stimulus electrodes to a neural pathway in order to give rise to an evoked compound action potential (ECAP) on the neural pathway;
- measurement circuitry for recording a neural compound action potential signal sensed at the one or more sense electrodes; and
- a control unit configured to:
  - control application of a neural stimulus as defined by at least one stimulus parameter;
  - measure via the measurement circuitry a neural compound action potential response evoked by the stimulus;
  - determine from the measured evoked response a feedback variable;
  - complete a feedback loop by using the feedback variable to control the at least one stimulus parameter value; and
  - adaptively compensate for changes in a gain of the feedback loop caused by electrode movement relative to the neural pathway, by applying a compensating transfer function to the feedback variable, the compensating transfer function include the stimulus parameter as a variable and being configured to compensate for both (i) a distance-dependent transfer function of stimulation and (ii) a distance dependent transfer function of measurement which is distinct from the distance-dependent transfer function of stimulation;
  - wherein applying the compensating transfer function comprises multiplying the feedback variable with an exponentiated version ($I^k$) of the stimulus parameter (I) used to generate the ECAP.

17. The implantable device of claim 16, wherein the control unit is further configured to generate an error signal relative to a setpoint and feed the error signal into a controller which determines a future stimulus intensity.

18. A non-transitory computer readable medium for controllably applying a neural stimulus, comprising the following instructions for execution by one or more processors:
- computer program code means for applying the neural stimulus to a neural pathway in order to give rise to an evoked compound action potential (ECAP) on the neural pathway, the stimulus being applied as defined by at least one stimulus parameter;
- computer program code means for measuring a neural compound action potential response evoked by the stimulus and deriving from the measured evoked response a feedback variable;
- computer program code means for completing a feedback loop by using the feedback variable to control the at least one stimulus parameter value; and
- computer program code means for adaptively compensating for changes in a gain of the feedback loop caused by electrode movement relative to the neural pathway, by applying a compensating transfer function to the feedback variable, the compensating transfer function including the stimulus parameter as a variable and being configured to compensate for both (i) a distance-dependent transfer function of stimulation and (ii) a distance dependent transfer function of measurement which is distinct from the distance-dependent transfer function of stimulation;
- wherein applying the compensating transfer function comprises multiplying the feedback variable with an exponentiated version (Ik) of the stimulus parameter (I) used to generate that ECAP.

* * * * *